(12) United States Patent
Chen et al.

(10) Patent No.: US 10,596,118 B2
(45) Date of Patent: Mar. 24, 2020

(54) SOLID DISPERSIONS

(71) Applicant: Shionogi Inc., Florham Park, NJ (US)

(72) Inventors: Zhengming Chen, Belle Mead, NJ (US); Xiaoming Chen, Westfield, NJ (US); Kevin Halloran, Somerset, NJ (US)

(73) Assignee: Shionogi, Inc., Florham Park, NJ (US)

( * ) Notice: Subject to any disclaimer, the term of this patent is extended or adjusted under 35 U.S.C. 154(b) by 0 days.

(21) Appl. No.: 15/555,839

(22) PCT Filed: Mar. 10, 2016

(86) PCT No.: PCT/US2016/021671
§ 371 (c)(1),
(2) Date: Sep. 5, 2017

(87) PCT Pub. No.: WO2016/145138
PCT Pub. Date: Sep. 15, 2016

(65) Prior Publication Data
US 2018/0036245 A1 Feb. 8, 2018

Related U.S. Application Data

(60) Provisional application No. 62/131,060, filed on Mar. 10, 2015.

(51) Int. Cl.
| | | |
|---|---|---|
| *A61K 31/085* | (2006.01) | |
| *A61K 47/32* | (2006.01) | |
| *A61K 9/14* | (2006.01) | |
| *A61K 47/38* | (2006.01) | |

(52) U.S. Cl.
CPC ............ *A61K 9/146* (2013.01); *A61K 31/085* (2013.01); *A61K 47/32* (2013.01); *A61K 47/38* (2013.01)

(58) Field of Classification Search
None
See application file for complete search history.

(56) References Cited

U.S. PATENT DOCUMENTS

| | | | |
|---|---|---|---|
| 5,750,576 A | 5/1998 | DeGregorio et al. | |
| 5,912,273 A | 6/1999 | DeGregorio et al. | |
| 7,022,337 B2 | 4/2006 | Liang et al. | |
| 7,931,917 B2 | 4/2011 | Ryde et al. | |
| 8,034,381 B2* | 10/2011 | Moschwitzer | A61K 9/10 424/489 |
| 8,367,118 B2 | 2/2013 | Curatolo et al. | |
| 2002/0161032 A1 | 10/2002 | Guivarc'h et al. | |
| 2005/0187301 A1* | 8/2005 | Lehtola | A61K 9/1652 514/720 |
| 2005/0227966 A1* | 10/2005 | Shah | A61K 9/146 514/217.09 |
| 2006/0204588 A1* | 9/2006 | Liversidge | A61K 9/0019 424/490 |
| 2007/0104742 A1* | 5/2007 | Lehtola | A61K 9/08 424/400 |
| 2010/0015225 A1 | 1/2010 | Diederich et al. | |
| 2010/0028403 A1 | 2/2010 | Scheuermann et al. | |
| 2011/0014282 A1 | 1/2011 | de Vasconcelos | |
| 2011/0018154 A1 | 1/2011 | Janssens et al. | |
| 2013/0123353 A1 | 5/2013 | Sun et al. | |
| 2013/0224301 A1 | 8/2013 | Curatolo et al. | |
| 2013/0231350 A1 | 9/2013 | Padval et al. | |
| 2013/0303628 A1 | 11/2013 | Breitenbach et al. | |
| 2013/0345320 A1 | 12/2013 | Kolter et al. | |
| 2016/0000732 A1 | 1/2016 | Kulkarni et al. | |

FOREIGN PATENT DOCUMENTS

| | | |
|---|---|---|
| CN | 1953741 A | 4/2007 |
| EP | 0901786 B1 | 6/2007 |
| JP | 2011-513301 A | 4/2011 |
| JP | 2011-515444 A | 5/2011 |
| WO | 2005/079777 A1 | 9/2005 |
| WO | 2009/158584 A1 | 12/2009 |
| WO | 2013/040187 A1 | 3/2013 |

OTHER PUBLICATIONS

Chokshi et al., "Improving the Dissolution Rate of Poorly Water Soluble Drug by Solid Dispersion and Solid Solution-Pros and Cons," Drug Delivery, 14:33-45, 2007.*
Nikghalb et al., "Solid Dispersion: Methods and Polymers to increase the solubility of poorly soluble drugs," Journal of Applied Pharmaceutical Science vol. 2 (10), pp. 170-175, Oct. 2012.*
Gülsün et al., "Nanocrystal Technology for Oral Delivery of Poorly Water-Soluble Drugs," Fabad J. Pharm. Sci., 34, 55-65, 2009.*
Junghanns et al., "Nanocrystal technology, drug delivery and clinical applications," International Journal of Nanomedicine 2008:3(3) 295-309.*
International Search Report and Written Opinion dated May 26, 2016 for International Application No. PCT/US2016/021671, 9 pages.
Curatolo et al., "Utility of Hydroxypropylmethylcellulose Acetate Succinate (HPMCAS) for Initiation and Maintenance of Drug Supersaturation in the GI Milileu", Pharmaceutical Research, Jun. 2009, vol. 26, No. 6, pp. 1419-1431.
Friesen et al., "Hydroxypropyl Methylcellulose Acetate Succinate-Based Spray-Dried Dispersions: An Overview", Molecular Pharmaceutics, 2008, vol. 5, No. 6, pp. 1003-1019.

(Continued)

*Primary Examiner* — Jared Barsky
(74) *Attorney, Agent, or Firm* — MH2 Technology Law Group, LLP

(57) ABSTRACT

An ospemifene solid dispersion for enhancing solubility and bioavailability, and methods of preparation thereof are disclosed. The solid dispersion comprises an active pharmaceutical ingredient, such as ospemifene, and a hydfophilie carrier, such as copovidone, hypromellose acetate succinate, polyvinylpyrrolidine, a polyvinylpyrrolidine/vinyl acetate co-polymer, hydroxyl propyl methylcellulose, hypromellose acetate succinate, a Eudragit® compound, hydroxypropyl-cellulose, a polyvinyl caprolactam-polyvinyl acetate polyethylene glycol graft co-polymer, hydroxypropyl methylcellulose phthalate, and mixtures thereof, and optionally a surfactant The ospemifene solid, dispersions can be used in methods of treating a symptom related, to menopause, such as vaginal dryness or sexual dysfunction, or in methods of treating osteoporosis.

13 Claims, 15 Drawing Sheets

(56) References Cited

OTHER PUBLICATIONS

Huang et al., "Fundamental aspects of solid dispersion technology for poorly soluble drugs", Acta Pharmaceutica Sinica B, 2014, vol. 4, No. 1, pp. 18-25.
Janssens et al., "Review: physical chemistry of solid dispersion", Journal of Pharmacy and Pharmacology, 2009, vol. 61, pp. 1571-1586.
Lakshman et al., "Application of Melt Extrusion in the Development of a Physically and Chemically Stable High-Energy Amorphous Solid Dispersion of a Poorly Water-Soluble Drug", Molecular Pharmaceutics, 2008, vol. 5, No. 6, pp. 994-1002.
Leuner et al., "Improving drug solubility for oral delivery using solid dispersions", European Journal of Pharmaceutics and Biopharmaceutics, 2000, vol. 50, pp. 47-60.
Abu T.M. Serajuddin, "Solid Dispersion of Poorly Water-Soluble Drugs: Early Promises, Subsequent Problems, and Recent Breakthroughs", Journal of Pharmaceutical Sciences, Oct. 1999, vol. 88, No. 10, pp. 1058-1066.
Sun et al., "Enhanced kinetic solubility profiles of indomethacin amorphous solid dispersions in poly(2-hydroxyethyl methacrylate) hydrogels", European Journal of Pharmaceutics and Biopharmaceutics, 2012, vol. 81, pp. 149-158.
Tanno et al., "Evaluation of Hypromellose Acetate Succinate (HPMCAS) as a Carrier in Solid Dispersions", Drug Development and Industrial Pharmacy, 2004, vol. 30, No. 1, pp. 9-17.
Carsten Timpe, "Drug Solubilization Strategies Applying Nanoparticulate Formulation and Solid Disperson Approaches in Drug Development", American Pharmaceutical Review, 2010, vol. 13, pp. 12-21.
Vasconcelos et al., "Solid dispersions as strategy to improve oral bioavailability of poor water soluble drugs", Drug Discovery Today, Dec. 2007, vol. 12, No. 23/24. pp. 1068-1075.

Australian Examination Report No. 1 for Australian Patent Application No. 2016229086 dated Apr. 20, 2018, 8 pages.
Tran, T.H. et al., 'Preparation and evaluation of raloxifene-loaded solid dispersion nanoparticle by spray-drying technique without an organic solvent', International Journal of Pharmaceutics, 2013, vol. 443, No. 1-2, pp. 50-57.
Tran, T.H. et al., 'Development of raloxifene-solid dispersion with improved oral bioavailability via spray-drying technique', Archives of Pharmacal Research, 2013, vol. 36, No. 1, pp. 86-93.
Wu et al., "The role of biopharmaceutics in the development of a clinical nanoparticle formulation of MK-0869: a Beagle dog model predicts improved bioavailability and diminished food effect on absorption in human" International Journal of Pharmaceutics, vol. 285, Issues 1-2, Nov. 5, 2004, pp. 135-146.
Japanese Office Action for Japanese Patent Application No. 2017-548065 dated Aug. 28, 2018, 9 pages with English translation.
"Assessment report, Senshio, Procedure No. EMEA/H/C/002780/0000", European Medicines Agency, Nov. 20, 2014, 59 pages.
First Office Action and Search Report dated Aug. 27, 2019 for Chinese Patent Application No. 201680014749.9, 32 pages with English translation.
Wang Liang, "Study on solid dispersion of nitredipine", China Doctoral Dissertations Full-text Database (electronic journal), Volume of medical and health science, Mar. 31, 2011, vol. 3, E079-12, 4 pages (See p. 3 (paragraphs 3-4), p. 4 (paragraph 3), and p. 7 (paragraphs 2-3), of the translation of Chinese Office Action dated Aug. 27, 2019 for a concise explanation of the relevance of this document, which is referred to as D2 in the Office Action).
Ren Xiuhua, "Application and Progress of Solid Dispersions in Pharmaceutics", Herald of Medicine, Feb. 25, 2003, vol. 22, No. 2, pp. 110-112 (See p. 4 (paragraphs 4-5), of the translation of Chinese Office Action dated Aug. 27, 2019 for a concise explanation of the relevance of this document, which is referred to as D2 in the Office Action).

\* cited by examiner

SOLID DISPERSIONS

CROSS-REFERENCE TO RELATED APPLICATIONS

This application is a U.S. National Stage application of PCT/US2016/021671 filed 10 Mar. 2016, which claims the benefit of, and relies on the filing date of, U.S. provisional patent application No. 62/131,060, filed 10 Mar. 2015, the entire disclosure of which is incorporated herein by reference.

FIELD

This application relates generally to solid dispersions comprising an active pharmaceutical ingredient, such as ospemifene, and a hydrophilic carrier, and optionally one or more excipients, including, but not limited to a surfactant, and methods of making and using the same.

BACKGROUND

In the field of pharmaceuticals, oral dosage forms of drugs are a preferred method of delivery for a variety of reasons. Generally, active pharmaceutical ingredients (APIs) supplied, in oral dosage form are easier to manufacture, dispense and administer. Manufacture is made simpler and more consistent due to the existence of well-established techniques for producing consistent doses in forms that can be chemically very stable. Dispensing and administration are simpler since oral dosages can typically be self-administered, as opposed to other forms such as intravenously supplied drugs, which are more difficult to administer, or which may require a trained professional in order to properly administer to a patient in need of the therapeutic moiety.

Recently, advances in chemistry and drug design methodologies have led to the discovery of a number of new drug candidates. For example, high throughput screening and combinatorial chemistry are very efficient at selecting candidate drugs based on specific binding to a target of interest. Target specificity is highly desirable in therapeutic agents given that in general it also correlates with an increase in therapeutic index, the ratio between the $LD_{50}$ for a particular compound, and the levels required in order to achieve the desired therapeutic effect. However, one of the drawbacks of these developmental strategies is that they fend to select for compounds that are not optimal in terms of drug delivery properties, leading to impediments in moving candidate compounds to the later stages of development.

Thus, one of the limitations in newer approaches to development of novel pharmaceuticals is that new chemical entities may not always have the desired properties that would make them excellent candidates for oral administration, notwithstanding the fact that the active ingredient may possess significant therapeutic potential.

Recent experience has shown that many new APIs are poorly water-soluble and not well absorbed after administration (See for example: Charman & Charman, 2003; van Drooge et al., 2006). Limitations in the rate of solubilization and absorption will have a direct impact on bioavailability and pharmacokinetic performance of any compound. Thus, in many cases, it will be desirable to improve upon the solubility properties of an API in order to reduce the time before therapeutically effective levels are achieved in the patient, as well to improve the overall uptake of the pharmaceutical in the systemic-circulation, or whatever compartment the drug is intended to reach in order to exert its therapeutic effects.

The production of solid drug dispersions is one method available to improve solubility and dissolution of poor water-soluble drugs (Vasconcelos et al., 2007). The enhancement of solubility and dissolution may lead to the increase of bioavailability and/or permit the use of a reduced dose for drugs with poor water solubility. However, limitations of solid dispersion technology include, but are not limited by, laborious and expensive methods of preparation, reproducibility of physicochemical characteristics, difficulty in incorporating into formulation of dosage forms, scale-up of manufacturing process, and stability of the drug and vehicle.

SUMMARY

The present disclosure provides solid dispersions and compositions comprising the same. The solid dispersions comprise a poorly water soluble drug, such as ospemifene, and a hydrophilic carrier, including, but not limited to at least one of polyvinylpyrrolidine (also known as povidone or PVP) (e.g., PVP K30), Polyvinylpyrrolidine/vinyl acetate co-polymers (also known as copovidone or PVPVA) (e.g., PVPVA64, also known as, Kollidon® VA64), hydroxyl propyl methylcellulose (HPMC), hypromellose acetate succinate (HPMCAS), Eudragit® compounds (a methacrylic acid copolymer, e.g., Eudragit® L100-55), hydroxypropyl-cellulose (HPC) (e.g., HPC-SL), polyvinyl caprolactam-polyvinyl acetate polyethylene glycol graft co-polymers (e.g., Soluplus®), and hydroxypropyl methylcellulose phthalate (HPMCP) (e.g., HP-55), or a mixture thereof. In some embodiments, the ratio of ospemifene to the hydrophilic carrier is in a range of about 1:1 to about 1:20 (w/w). In some embodiments, the ratio of ospemifene to the hydrophilic carrier is about 1:4 (w/w).

In addition to a hydrophilic carrier, the solid dispersion may further comprise one or more surfactants, including, for example, polysorbates (e.g., Tween® 20, Tween® 80, Span® 20, Span® 80), sodium docusate (e.g., AOT), and poloxamers (e.g., poloxamer 407).

Another aspect is directed to an aqueous solution, comprising a solid dispersion dissolved in a solvent selected from water, 0.1N HCl, or a buffered solution haring a pH in a range from about 6.5 to about 7.5, wherein the solid dispersion comprises ospemifene and a hydrophilic carrier as described herein.

Yet another aspect is directed to methods of making solid dispersions of poorly water-soluble drugs, such as ospemifene, including melting and solvent evaporation methods. In one embodiment, the method of preparing a solid dispersion of ospemifene, comprises: dissolving ospemifene in a first solvent, to produce a ospemifene solution; dissolving a hydrophilic carrier in a second solvent, to produce a hydrophilic carrier solution; combining the ospemifene solution and the hydrophilic carrier solution to produce on admixture; subjecting the admixture to drying conditions to remove the first solvent and second solvent from the admixture, such that the remaining material forms a solid dispersion of ospemifene and the hydrophilic carrier.

In certain embodiments of these methods, the hydrophilic carrier is chosen from the group consisting of copovidone, hypromellose acetate succinate, polyvinylpyrrolidine, a polyvinylpyrrolidine/vinyl acetate co-polymer, hydroxyl propyl methylcellulose, a Eudragit® compound (a methacrylic acid copolymer), hydroxypropylcellulose, a polyvinyl caprolactam-polyvinyl acetate polyethylene glycol graft co-polymer, hydroxypropyl methylcellulose phthalate, and mixtures thereof.

In certain embodiments of these methods, the first solvent comprises a solvent selected from the group consisting of methanol or ethanol. In certain embodiments of these methods, the second solvent comprises a solvent selected from the group consisting of water, methanol, or ethanol. In certain embodiments of these methods, the first and second solvent are the same.

In certain embodiments of these methods, the ratio of ospemifene to the hydrophilic carrier in the admixture ranges from 1:1 to 1:20 (w/w). In certain embodiments of these methods, the ratio of ospemifene to the hydrophilic carrier in the admixture is between 1:2 to 1:4 (w/w).

In certain embodiments, the methods further comprise a step of dissolving a surfactant in a third solvent to produce a surfactant solution and combining the surfactant solution with the ospemifene solution and hydrophilic solution to produce an admixture. In certain embodiments, the third solvent comprises a solvent selected from the group consisting of water, methanol, or ethanol.

In certain embodiments, the drying conditions comprise conditions of ambient temperature and ambient atmospheric pressure for a period of up to about 90 hours. In other embodiments, the drying conditions comprise a condition of reduced atmospheric pressure and a period of time of less than 90 hours.

Another aspect is directed to pharmaceutical compositions comprising a solid dispersion of a poorly water-soluble drug, such as ospemifene, a hydrophilic carrier, including, but not limited to, povidone, copovidone, HPMC, HPMCAS, Eudragit® compounds (methacrylic acid copolymers), polyvinyl caprolactam-polyvinyl acetate polyethylene glycol graft co-polymers, and hydroxypropyl methylcellulose phthalate (HPMCP), a pharmaceutically acceptable excipient, and optionally a surfactant. In certain embodiments, the composition is provided in a dosage form. In certain embodiments, the pharmaceutically acceptable excipient comprises at least one of a glidant, a dispersant, an enteric coating, a lubricant, a binder, or a buffering agent. In certain embodiments, the pharmaceutically acceptable excipient is selected from at least one of colloidal silicon dioxide, lactose monohydrate, magnesium stearate, mannitol, microcrystalline cellulose, polyethylene glycol, pregelatinized starch, sodium starch glycolate, titanium dioxide, triacetin, and triose, and mixtures thereof. In certain embodiments, the hydrophilic carrier and surfactant are combined in a ratio ranging from 1:1 to 1:6. In some embodiments the pharmaceutical composition is provided in a dosage form selected from a tablet, a capsule, or a powder. In certain embodiments, after a single administration in a human subject of the pharmaceutical composition there is greater bioavailability or no substantial difference in the bioavailability of ospemifene when the composition is administered to the subject in a fasted versus a fed state.

The present disclosure further provides a method of treating a symptom related to menopause, the method comprising administering to a patient a pharmaceutical composition comprising a solid dispersion dosage form comprising ospemifene and a hydrophilic carrier including, but not limited to, povidone, copovidone, HPMC, HPMCAS, Eudragit® compounds (methacrylic acid copolymers), polyvinyl caprolactam-polyvinyl acetate polyethylene glycol graft co-polymers, and hydroxypropyl methylcellulose phthalate (HPMCP) or mixtures thereof, and optionally a surfactant, in an amount sufficient to treat the symptom related to menopause. In some embodiments the symptom related to menopause is vaginal dryness or sexual dysfunction.

Another aspect is directed to methods of treatment, including methods of treating a symptom related to menopause, the method comprising administering the pharmaceutical composition, as described herein, to a patient in an amount sufficient to treat the symptom related to menopause. In certain embodiments, the symptom related to menopause is a sexual dysfunction. In certain embodiments, the sexual dysfunction is selected from the group consisting of desire disorder, arousal disorder, orgasmic disorder, vaginal dryness, and dyspareunia. Other embodiments are directed to methods of treating osteoporosis, the methods comprising administering the pharmaceutical composition, as described herein, to a patient in an amount sufficient to treat osteoporosis.

In certain embodiments, the pharmaceutical composition is administered at a dosage of less than 60 mg ospemifene per day. In certain embodiments, the pharmaceutical composition is administered without food.

BRIEF DESCRIPTION OF THE DRAWINGS

The accompanying drawings, which are incorporated in and constitute a part of this specification, illustrate certain embodiments, and together with the written description, serve to explain certain principles of the compositions and methods disclosed herein.

DETAILED DESCRIPTION

Figure 1:
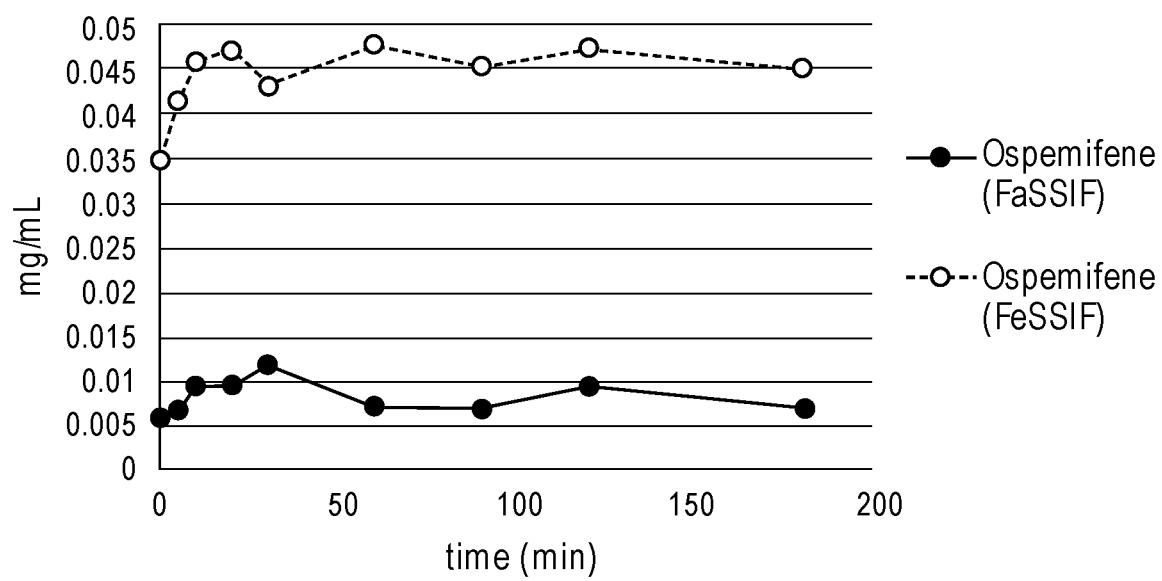
FIG. 1 depicts the dissolution kinetics of ospemifene alone (target concentration of 0.24 mg/mL) in FeSSIF and FaSSIF.

Reference will now be made in detail to various exemplary embodiments, examples of which are illustrated in the accompanying drawings and discussed in the detailed description that follows. It is to be understood that the following detailed description is provided to give the reader a fuller understanding of certain embodiments, features, and details of aspects of the invention, and should not be interpreted as limiting the scope of the invention.

1. Definitions

In order that the present invention may be more readily understood, certain terms are first defined. Additional definitions are set forth throughout the detailed description.

The terms "subject," "host," "patient," and "individual" are used interchangeably herein to refer to any mammalian subject for whom diagnosis or therapy is desired, particularly humans.

The term "active pharmaceutical ingredient" or "API" refers to a substance intended to be used as a component of a drug, and to furnish pharmacological activity or other direct effect in the diagnosis, cure, mitigation, treatment, or prevention of disease, or to affect the structure or any function of the organism to which it is administered. It includes any substance intended for final crystallization, purification or salt formation, or any combination of these activities to become a substance or mixture used to furnish pharmacological activity or other direct effect in the diagnosis, cure, mitigation, treatment, or prevention of disease, or to affect the structure or any function of the organism to which it is administered.

The term "Eudragit® compound" refers to a methacrylic copolymer, such as an amino alkyl methacrylic copolymer (immediate release), a methacrylic acid copolymer (delayed release), a methacrylic ester copolymer (time-controlled release), or an ammonioalkyl methacrylate copolymer (time-controlled release), that can be used in drug formulation to affect the release profile of the drug or API. Eudragit® L100-55 is a copolymer of methacrylic acid and ethyl acrylate (1:1). Based on SEC method the weight average molar mass (Mw) of EUDRAGIT® L100-55 is approx. 320,000 g/mol. Eudragit® L100 is a copolymer of methacrylic acid and methyl methacrylate (1:1). Eudragit® S100 is a copolymer of methacrylic acid and methyl methacrylate (1:2). Eudragit® L30 D-55 is an aqueous dispersion (30% of dry product) of a copolymer of methacrylic acid and ethyl acrylate (1:1). Eudragit® FS 30D is an aqueous dispersion (30% of dry product) of a copolymer of methyl acrylate, methyl methacrylate, and methacrylic acid.

The term "ospemifene" refers to the Z-isomer of the compound of formula (I):

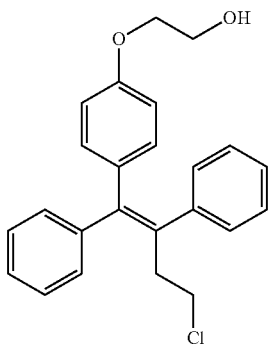

(I)

and pharmaceutically acceptable salts thereof.

As used herein, the term "amorphous" means, for example, when applied to the API of a solid dispersion, that the crystalline fractions of API are less than about 5% by weight, based on the total weight of the solid dispersion.

As used herein, a "solid dispersion" is defined as a molecular mixture of an API and one or more hydrophilic carriers, where the hydrophilic carrier functions to increase the solubility of the API. The API may be dispersed as amorphous clusters or crystalline particles in the matrix or the API may be molecularly dispersed throughout the matrix. A solid dispersion is prepared by converting a fluid drug-carrier combination to the solid state, generally by a melting or solvent evaporation process, as is known in the art, or by anti-solvent coprecipitation. Different types of solid dispersions can be distinguished based on their molecular arrangements. These different types of solid dispersions include, but are not limited to, (1) eutectic mixtures; (2) amorphous precipitates in crystalline matrix; (3) solid solutions, including continuous solid solutions, discontinuous solid solutions, substitutional solid solutions, and interstitial solid solutions; (4) glass suspension where matrix is in amorphous state and API is dispersed as crystalline particles in the matrix; (5) glass suspension where matrix is in amorphous state and API is dispersed as amorphous clusters in the matrix; and (6) glass solution where matrix is in amorphous state and API is molecularly dispersed throughout the matrix. The dispersion of an API in a hydrophilic carrier by mechanical mixing is not encompassed by this definition.

2. Poorly Water Soluble Drugs

Along with permeability, solubility and properties of a drug are one factor in determining bioavailability of an oral dosage form. A number of well-known compounds have solubility characteristics that present challenges for oral administration. These include such compounds as griseofulvin, digoxin, phenytoin, and chloramphenicol. More recently, the advent of high-throughput screening methods, while providing increased specificity between candidate compounds and their predicted targets, comes at a cost, that being that in general these compounds are poorly water-soluble. One technique that has been used to improve solubility is micronization, where particle size is reduced in order increase the apparent surface area of the API. However, very fine particles create other problems including difficulty in handling, and reduced wettability. Attempts to overcome these limitations such as the use of organic solvents or surfactants may lead to reduced tolerability and other problems related to the mechanics of manufacturing or the economics of producing the drug.

One drug that displays relatively low solubility is ospemifene, a selective estrogen receptor modulator (SERM) (Kangas, 1990). Ospemifene, is the Z-isomer of the compound of formula (I):

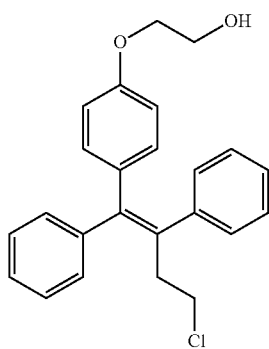

(I)

It is one of the primary metabolites of toremifene, and has been shown to have estrogen agonist and antagonist activity (Kangas. 1990 and U.S. Pat. No. 6,245,819, both of which are incorporated by reference in their entirety).

Ospemifene has been shown to possess anti-osteoporotic activity, and decreases total and LDL cholesterol both in experimental model systems and human volunteers (U.S. Pat. Nos. 5,750,576 and 6,037,379; the entireties of which are incorporated by reference). This compound has also been shown to have anti-tumor activity at an early stage of breast cancer development in an experimental animal model system.

Ospemifene is also the first SERM to be shown to have beneficial effects in treating climacteric syndromes (menopause) in healthy women. During and after menopause, women often develop symptoms generally related to estrogen deficiency. These can include hot flashes, sweating, insomnia, depression, vaginal dryness, urinary incontinence, nausea, pain, osteoporosis, coronary heart disease, breast tenderness, edema, fatigue, decreased sexual activity, as well as later psychological issues (Payer, 1990; Rekers, 1991). Administration of estradiol has been a traditional treatment for these symptoms and it is effective in mitigating the effects of menopause. However, given that the normal function of estrogen is that of a steroid hormone receptor agonist, its therapeutic administration can result in undesirable side effects such as an increase in risk of developing endometrial and breast cancers. In some cases these risks can be tempered by sequential progestin administration, but the risk of breast cancer is not diminished even with progestin.

Previous studies with ospemifene showed that the compound could be useful for treatment of a variety of symptoms including, for example, vaginal dryness and sexual dysfunction (International Patent Publication WO 02/07718; U.S. Pat. No. 6,245,819; the entire disclosures of which are incorporated by reference herein). Trials in humans indicated that a daily dose in a range from about 25 mg to about 100 mg, and in particular about 60 mg, was effective to alleviate vaginal dryness and improve sexual activity. Ospemifene was also shown to have a superior profile of estrogenic and anti-estrogenic effects, as compared to other anti-estrogens or SERMs. In addition, because of its ability to interact with the estrogen receptor, it is expected that ospemifene may be effective in treating osteoporosis.

However, one of the limitations encountered with ospemifene is that it is highly lipophilic and as a result not particularly water-soluble. This low inherent water solubility means that greater amounts of the compound must be administered in order to achieve therapeutically effective levels in the patient. Similarly, low solubility would be expected to reduce overall bioavailability, contributing to the delay in the time from which the drug is administered until it reaches its target tissues. Consequently, the currently recommended daily dose of presently available oral dosage forms is 60 mg. Even at such doses, pharmacokinetic studies have shown that the majority of ospemifene is eliminated via the fecal route, suggesting that only a minor fraction of the ingested dose actually becomes bioavailable (Koskimies et al., 2013). Consequently, it would be highly advantageous to provide a form of ospemifene with enhanced solubility properties in order to improve its bioavailability profile.

3. Solid Dispersions

It is also well known that lipophilic compounds, like ospemifene, usually exhibit low solubility in aqueous solutions. With respect to the use of lipophilic compounds as potential therapeutic agents, low solubility in aqueous solutions can result in poor bioavailability. Often, one approach is to use larger doses in order to achieve therapeutically effective levels of the API in the patient, an approach that can lead to the increased cost of providing more API than might actually be necessary to achieve the desired therapeutic result.

One strategy in the field of pharmaceutical compounding for overcoming the limitations posed by poorly water-soluble compounds is the synthesis of a solid dispersion form of a drug (See for example: Vasconcelos et al., 2007; Leuner & Dressman, 2000; Jansenns & Mooter, 2009; and Serajuddin, 1999).

In general then, solid dispersions function to enhance the solubility and dissolution of lipophilic drugs. In turn, the expectation is that by enhancing solubility and dissolution, an increase in bioavailability and/or reduced dose requirements can be achieved for drugs normally exhibiting poor water solubility. In addition to enhanced solubility, the presence of a hydrophilic carrier may improve wettability, which also benefits dissolution. Normally, dissolution of drugs results in a local environment where the API is at a super-saturated concentration, which favors precipitation and/or crystallization, so improved dissolution alone does not fully address the problem of effectively delivering lipophilic compounds. Conveniently, the hydrophilic carriers typically used in solid dispersion forms also enhance the kinetic solubility of a compound by maintaining it in an amorphous state, thus preventing drug crystallization during dissolution.

Hydrophilic carriers suitable for preparing pharmaceutical solid dispersions of ospemifene include, but are not limited to, polyethylene glycol (PEG), preferably with MW from about 1.5-20 kDa; povidone, also known as polyvinylpyrrolidone (PVP), preferably with MW from about 2.5 to 3,000 kDa; polyvinyl alcohol (PVA); crospovidone; polyvinylpyrrolidone polyvinyl acetate copolymer (copovidone); hydroxylpropylmethylcellulose (HPMC, Hypromellose), preferably with MW from about 10 to 1,500 kDa; methyl cellulose; copolymers of ethylene oxide and propylene oxide (PEO/PPO); hydroxypropylcellulose (HPC); carboxymethylethylcellulose; hypromellose succinate acetate (HPMCAS); hydroxypropylmethylcellulose phthalate (HPMCP); polyacrylates and polymethacrylates; Eudragit® compounds; Kollidon® VA64; cyclodextrins; surfactants (e.g., inulin, inutec SP1, compritol 888, gelucire 44/14, poloxamer 407); superdisintegrants (e.g., Explotab, sodium croscarmellose); polyols; sugars; urea. See also for example: Leuner & Dressman, 2000; U.S. Patent Publication No. 2013/0123353, the entire disclosures of which are incorporated by reference herein. The MW of the hydrophilic carriers, where appropriate (e.g., PEG, povidone), is determined using methods known to a person of ordinary skill in the art, as such methods are typically applied to the molecules in question.

In various exemplary embodiments, the hydrophilic carrier is selected from at least one of polyvinylpyrrolidine (also known as povidone or PVP) (e.g., PVP K30), Polyvinylpyrrolidine/vinyl acetate co-polymers (also known as copovidone or PVPVA) (e.g., PVPVA64; Kollidon® VA64), hydroxyl propyl methylcellulose (HPMC), hypromellose acetate succinate (HPMCAS), Eudragit® compounds (e.g., Eudragit® L100-55, Eudragit® S100, Eudragit® L30 D-55, Eudrugit® FS 30D), hydroxypropylcellulose (HPC) (e.g., HPC-SL), polyvinyl caprolactam-polyvinyl acetate polyethylene glycol graft co-polymers (e.g., Soluplus®), and Hydroxypropyl methylcellulose phthalate (HPMCP) (e.g., HP-55).

In some cases, it will be advantageous to vary the ratio of drug to hydrophilic carrier in order to optimally affect the performance of the drug. For example, in the case of ospemifene, ospemifene can be combined with hydrophilic carriers as described herein (e.g., including, but not limited to, povidone, copovidone, HPMC, HPMCAS, Eudragit® compounds, polyvinyl caprolactam-polyvinyl acetate polyethylene glycol graft co-polymers, and HPMCP or mixtures thereof) in a ratio ranging from about 2:1 to about 1:50 (w/w), about 1:1 to about 1:20 (w/w), from about 1:1 to about 1:15 (w/w), from about 1:1 to about 1:10 (w/w), from about 1:1 to about 1:5 (w/w), from about 1:2 to about 1:5, or from about 1:2 to about 1:4 (w/w). In one embodiment, the ratio of ospemifene to hydrophilic carrier is about 1:4 (w/w).

In certain embodiments, the solid dispersion may further comprise one or more surfactants. The surfactant may be non-ionic, anionic, cationic, amphoteric or zwitterionic.

Examples of suitable non-ionic surfactants include ethoxylated triglycerides; fatty alcohol ethoxylates; alkylphenol ethoxylates; fatty acid ethoxylates; fatty amide ethoxylates; fatty amine ethoxylates; sorbitan alkanoates; ethylated sorbitan alkanoates; alkyl ethoxylates; Pluronics™; alkyl polyglucosides; stearol ethoxylates; alkyl polyglycosides.

Examples of suitable anionic surfactants include alkylether sulfates; alkylether carboxylates; alkyl benzene sulfonates; alkylether phosphates; dialkyl sulfosuccinates; sarcosinates; alkyl sulfonates; soaps; alkyl sulfates; alkyl carboxylates; alkyl phosphates; paraffin sulfonates; secondary n-alkane sulfonates; alpha-olefin sulfonates; isethionate sulfonates.

Examples of suitable cationic surfactants include fatty amine salts; fatty diamine salts; quaternary ammonium compounds; phosphonium surfactants; sulfonium surfactants; sulfoxonium surfactants.

Examples of suitable zwitterionic surfactants include N-alkyl derivatives of amino acids (such as glycine, betaine, aminopropionic acid); imidazoline surfactants; amine oxides; amidobetaines.

Non-limiting examples of a surfactant that can be used in the ospemifene solid dispersions, include, for example. Tween 20, Tween 80, Span 20, Span 80, sodium docusate (e.g., AOT), sodium lauryl sulfate, and poloxamers (e.g., poloxamer 407, Kolliphor® EL, Pluronic F68). Poloxamers are also known by the trade names Synperonics®, Pluronics®, and Kolliphor®/Cremophor®.

In some cases, it will be advantageous to vary the ratio of hydrophilic carrier and surfactant in order to optimally affect the performance of the drug. For example, in the case of solid dispersions of ospemifene, hydrophilic carriers, as described herein, can be combined with surfactants, as described herein, in a ratio ranging from about 1:1 to about 10:1 (w/w), from about 1:1 to about 6:1 (w/w), from about 1:1 to about 5:1 (w/w), from about 1:1 to about 4:1 (w/w), from about 1:1 to about 3:1, or from about 1:1 to about 2:1 (w/w). In one embodiment, the ratio of hydrophilic carrier to surfactant is about 6:1 (w/w). In another embodiment, the ratio of hydrophilic carrier to surfactant is about 1:1 (w/w).

In some cases, it will be advantageous to vary the ratio of drug, hydrophilic carrier, and surfactant in order to optimally affect the performance of the drug. For example, in the case of solid dispersions of ospemifene, ospemifene can be combined with hydrophilic carriers, as described herein, and surfactants, as described herein, in a ratio ranging from about 1:2-4:0.5-4 (w/w). In one embodiment, the ratio of ospemifene to hydrophilic carrier to surfactant is about 1:3.4:0.6 (w/w/w). In another embodiment, the ratio of ospemifene to hydrophilic carrier to surfactant is about 1:2:2 (w/w/w).

4. Pharmaceutical Compositions

The solid dispersions of ospemifene and a hydrophilic carrier can be prepared as a pharmaceutical composition. Suitable preparation forms for the pharmaceutical compositions disclosed herein include, for example, tablets, capsules, soft capsules, granules, powders, suspensions, emulsions, microemulsions, nanoemulsions, unit dosage forms, rings, films, suppositories, solutions, creams, syrups, transdermal patches, ointments and gels.

In certain embodiments, the pharmaceutical compositions disclosed herein may be produced via wet or dry granulation. Granulation is a process wherein primary powder particles are made to adhere to form larger, multi-particle entities known as granules. Pharmaceutical granules typically have a size ranging from about 0.2 mm to about 4.0 mm, depending on their subsequent use. For example, in the production of tablets or capsules, granules may be made as an intermediate product and may in certain embodiments have a size ranging from about 0.2 to about 0.5 mm.

Granulation methods can be divided in two types: wet granulation and dry granulation. In certain pharmaceutical compositions disclosed herein, at least one additional excipient may be added, such as diluents, to produce a unit dose weight of a suitable size, and disintegrating agents, which are added to aid the break-up of the granule when it reaches a liquid medium, e.g. on ingestion by the patient. Moreover, adhesives such as those in the form of a dry powder may also be added, for example if dry granulation is employed. The additional excipients may be mixed before granulation. In certain embodiments, at least one of the additional excipients is a non-naturally occurring ingredient.

In the dry granulation methods disclosed herein, the primary powder particles may be aggregated under high pressure. There are two main processes: either a large tablet (known as a slug) is produced in a heavy-duty tabulating press, or the powder may be squeezed between two rollers to produce a sheet of material (known as roller compaction). These intermediate products may be broken by any suitable milling technique. Dry granulation processes may be used for drugs that are sensitive to moisture.

Wet granulation processes involve the massing of a mix of dry primary powder particles using a granulating fluid. The fluid may contain a non-toxic solvent that is volatile so that it can be removed by drying. Typical liquids may include, for example, at least one of water, ethanol, and isopropanol. The granulation liquid may be used alone or as a solvent containing a dissolved adhesive (binder) that may be used to ensure particle adhesion once the granule is dry. The wet mass is then forced through a sieve to produce wet granules, which are then dried. A subsequent screening stage breaks agglomerates and removes the fine material.

In vitro dissolution testing may serve as a tool for characterizing the biopharmaceutical quality of a product at different stages in its lifecycle. In early drug development in vitro dissolution properties are supportive for choosing between different alternative formulation candidates for further development and for evaluation of active ingredients/drug substances. Moreover, in vitro dissolution data may be of importance when assessing changes in production site, manufacturing process or formulation and assist in decision concerning the need for bioavailability studies.

Drug absorption from a solid dosage form after oral administration depends on the release of the drug substance from the drug product, the dissolution or solubilization of the drug under physiological conditions, and the permeability across the gastrointestinal tract. In vitro dissolution may be relevant to the prediction of in vivo performance. Based on this general consideration, in vitro dissolution tests for solid dispersion oral dosage forms, such as tablets and capsules, may be used to a) assess the lot-to-lot quality of a drug product; b) guide development of new formulations; and c) ensure continuing product quality and performance after certain changes, such as changes in the formulation, manufacturing process, site of manufacture, and the scale-up of a manufacturing process.

In certain embodiments of the pharmaceutical compositions, after a single administration in a human subject of the ospemifene solid dispersion dosage form there is greater bioavailability or no substantial difference in the bioavailability of ospemifene when the formulation is administered to the subject in a fasted versus a fed state. In other words, in certain embodiments, food does not increase the bioavailability of the ospemifene solid dispersion dosage form, as it does with other ospemifene formulations, such as Osphena®, where bioavailability is significantly better in the fed state.

In the pharmaceutical composition according to certain embodiments disclosed herein, the intra-granular excipient may comprise at least one ingredient, which may belong to the same or different categories of excipients. For example, the intra-granular excipient may comprise at least one disintegrant, at least one diluent, and/or at least one binder. Accordingly, the intra-granular excipient may be a combination of at least one diluent and at least one binder; a combination at least one diluent and at least one disintegrant; a combination of at least one disintegrant and at least one binder; or a combination of at least one diluent, at least one disintegrant and at least one binder.

As typical non-limiting examples of the at least one disintegrant that may be added to the pharmaceutical composition according to embodiments disclosed herein, mention may be made of povidone, crospovidone, carboxymethylcellulose, methylcellulose, alginic acid, croscarmellose sodium, sodium starch glycolate, a starch (e.g., cornstarch, potato starch), formaldehyde-casein, alginic acid, silicon dioxide, guar gum and combinations thereof. In certain embodiments, at least one disintegrant is a non-naturally occurring ingredient.

As typical non-limiting examples of the at least one diluents that may be added to the pharmaceutical composition according to embodiments disclosed herein, mention may be made of a sugar (e.g., maltose, lactose, fructose, sucrose), a cellulosic material (e.g., microcrystalline cellulose, silicified microcrystalline cellulose, powdered cellulose), a starch (e.g., corn starch, pre-geletanized, maltodextrin, dextrin) a sugar alcohol (e.g., mannitol, sorbitol), a dextrate, calcium phosphate, a gum, an acrylate (e.g., polymethylacrylate), calcium carbonate, magnesium oxide, talc, and combinations thereof. In certain embodiments, at least one diluent is a non-naturally occurring ingredient.

As typical non-limiting examples of the at least one binder that may be added to the pharmaceutical composition according to embodiments disclosed herein, mention may be made of acacia, gelatin, carbomer, dextrin, starch (e.g., cornstarch), povidone, copovidone, carboxymethylcellulose, guar gum, glucose, hydroxypropyl cellulose, hydroxypropyl methylcellulose, methyl cellulose, ethyl cellulose, hypromellose acetate succinate, polymethacrylates, maltodextrin, hydroxyethyl cellulose, and combinations thereof. In certain embodiment, at least one binder is a non-naturally occurring ingredient.

The granulates can be made either by dry granulation or by wet granulation according to known technology. Suitable solvents in wet granulation may include, for example, water or ethanol.

The final pharmaceutical composition can be any suitable formulation such as tablets, capsules, granulates as such or granulates packaged into suitable dosage units, caplets, lozenges, and the like. The term "tablet" shall be understood to cover any kind of tablets, such as uncoated tablets, coated tablets, film-coated tablets, effervescent tablets, oral lyophilisates, orodispersable tablets, gastro-resistant tablets, prolonged-release tablets, modified-release tablets, chewable tablet, oral gums and pillules. The granulates shall be understood to cover also effervescent, gastro-resistant, prolonged-release and modified-release granulates. The capsules shall also be understood to cover gastro-resistant, prolonged-release and modified-release capsules.

The pharmaceutical composition disclosed herein may for example be a capsule comprising the granulates encapsulated in a shell made of gelatin or the like. The pharmaceutical composition may, in addition to the granulates, comprise at least one extra-granular lubricant. The at least one lubricant may be chosen, for example, from polyethylene glycol, sodium lauryl sulfate, calcium stearate, magnesium stearate, stearic acid, talc, vegetable oils, poloxamers, mineral oils, sodium lauryl sulphate, sodium stearyl fumarate, and zinc stearate. In certain embodiment, at least one lubricant is a non-naturally occurring ingredient. The pharmaceutical composition may also comprise other extra-granular excipients, such as diluents.

Alternatively, the pharmaceutical composition disclosed herein may be a tablet comprising the granulates in combination with at least one extra-granular excipient. The at least one extra-granular excipient may be chosen, for example, from disintegrants, diluents, binders, and lubricants. The at least one extra-granular disintegrant may also be one of the disintegrants mentioned above or combinations thereof. Similarly, the extra-granular diluents, binders, and lubricants can be selected from those mentioned above.

In certain embodiments of the pharmaceutical compositions disclosed herein, the active pharmaceutical ingredients, such as ospemifene, may be coated to ensure better chemical stability, reduce incompatibility, or aid in sustained release. For example, the pharmaceutical compositions disclosed herein may be formulated as an immediate release dosage form tablet or a controlled release dosage form tablet. At least one controlled release polymer such as hypromellose, polyethylene oxides, ethyl cellulose, ammonio methacrylate copolymers, and the like may be used in tablets to achieve a sustained release. In certain embodiments, the at least one controlled release polymer is a non-naturally occurring ingredient.

In certain embodiments disclosed herein, the pharmaceutical composition may also comprise other extra-granular ingredients such as flavoring agents, coloring agents, preservatives, suspending aids, and fillers. In certain embodiments, the extra-granular ingredient is a non-naturally occurring ingredient.

In certain embodiments disclosed herein, the granulates may optionally comprise at least one disintegrant ranging from about 0.1% to about 10%, such as about 0.1% to about 4%, by weight, of the granulates and/or at least one diluent ranging from about 20 wt % to about 80 wt % of the granulates.

If the granulates are processed into tablets, such tablets may contain at least one extra-granular disintegrant ranging from about 0.1% to about 25% by weight % of the tablet, at least one lubricant ranging from about 0.1% to about 2% by weight percent of the tablet, and at least one drug containing granulates ranging from about 20% to about 80% by weight percent of the tablet. The remaining part may comprise diluents optionally in combination with other ingredients such as binders, flavoring agents, coloring agents, preservatives, suspending aids, fillers and the like.

The particle size of the ospemifene in the granulates may be considered in order to get a good dissolution. For example, in certain embodiments, at least about 90% of the ospemifene drug substance may have a particle size less than about 250 micrometers, such as less than about 150 micrometers, or less than about 50 micrometers. In certain embodiments, about 50% of the ospemifene drug substance may have a particle size less than about 25 micrometers, such as less than about 15 micrometers. As used herein, the term "particle size" refers to the particle diameter, or in case the particles are not spherical, to the largest extension in one direction of the particle.

According to certain exemplary embodiments, pharmaceutical compositions disclosed herein may be in tablet form, comprising a core and at least one coating, wherein the core and optionally, the coating, comprises ospemifene.

According to certain exemplary embodiments, the coating of a tablet may comprise (a) at least one filler present in an amount ranging from about 5% to about 30% by weight of the pharmaceutical composition; (b) at least one binder present in an amount ranging from about 1% to about 10% by weight of the pharmaceutical composition; (c) at least one wetting agent present in an amount ranging from about 0.01% to about 2% by weight of the pharmaceutical composition: (d) at least one optional antioxidant present in an amount ranging from about 0% to about 2% by weight of the pharmaceutical composition; (c) ospemifene present in an amount ranging from about 0.1% to about 30%, such as about 0.1% to about 20%, by weight of the pharmaceutical composition; and (f) at least one optional chelating agent present in an amount ranging from about 0% to about 0.1% by weight of the pharmaceutical composition.

In certain embodiments, the coating may comprise at least one filler such as sucrose, at least one binder such as hydroxypropylmethylcellulose, at least one welting agent such as sucrose palmitate, optionally at least one antioxidant such as ascorbic acid or a salt thereof, and optionally at least one chelating agent such as EDTA.

Optionally, the pharmaceutical compositions disclosed herein may comprise a color coating. In certain embodiments, the color coating may comprise (a) optionally at least one filler present in an amount ranging from about 0.01% to about 8% by weight of the pharmaceutical composition; (b) optionally at least one binder present in an amount ranging from about 0.01% to about 2% by weight of the pharmaceutical composition; and (c) at least one coloring agent present in an amount ranging from about 0.01% to about 6% by weight of the pharmaceutical composition. In some embodiments, the at least one coloring agent is titanium dioxide.

In certain embodiments disclosed herein, the pharmaceutical composition may comprise a clear coating. The clear coating may, for example, be present in an amount ranging from about 0.01% to about 2% by weight of the pharmaceutical composition.

As disclosed herein, in certain embodiments the pharmaceutical composition may be in the form of a film. A pharmaceutical film for the administration of ospemifene and at least one compound for the treatment of hot flashes may be administered, for example, orally, topically, transdermally, or intravaginally.

A pharmaceutical film may comprise (a) at least one film-forming binder comprising hydrophilic polymers; (b) at least one dissolving polymeric material; and (c) an effective amount of at least one active pharmaceutical ingredient, such as ospemifene, wherein the at least one film-forming binder and the at least one dissolving polymeric material are effective to facilitate dissolution of the film within about 30 minutes following application of the film to a body surface, such as a moist body surface. Additionally, the pharmaceutical film may further comprise (a) at least one plasticizer to improve the mechanical properties of the film, such as tensile strength and elongation; (b) at least one surfactant as solubilizing, wetting or dispersing agents; (c) at least one coloring agent; and/or (d) at least one flavoring agent.

According to certain embodiments disclosed herein, the pharmaceutical composition may be in the form of a ring. The ring may be a spherical shaped device made of a pharmaceutically acceptable ingredient, such as comprising ospemifene. The ring may comprise silicone elastomers with, for example, dimethyl polysiloxane silanol, silica, and/or propyl orthosilicate added as needed. The ring structure may be multiple layers and may comprise a core containing the active ingredients), as well as an outer elastomer layer surrounding the core. The active ingredients) may be present in the ring as a solid solution, in amorphous form, as nanocrystals, crystals, or a combination thereof. The release pattern may be controlled by diffusion and may be tailored by the ring design, drug load, form of the active ingredient(s), and distribution of the active ingredients) in the ring. In certain embodiments, the ingredients may be pharmaceutically acceptable, biodegradable polymers such as polylactide, polyglycolic acid, and polylactic acid co-glycolic acid. The active ingredient(s) may be present in the polymer matrix and release may be controlled by the rate of polymer dissolution and degradation. The pharmaceutical composition in vaginal ring form may, for example, be manufactured by melt extrusion. The vaginal ring technology may offer a convenient delivery of ospemifene in a relatively constant rate over an extended period of time in a single application, such as every month, for example up to three months.

In additional embodiments disclosed herein, a pharmaceutical composition comprising ospemifene may be in gel form for intravaginal delivery and may comprise water and pharmaceutically acceptable ingredients. Examples of pharmaceutically acceptable ingredients such as mucoadhesive polymers that are capable of forming hydrogels may include, for example, synthetic polyacrylates, polycarbophil, chitosan, cellulose derivatives (such as hydroxyethylcellulose, hydroxypropylcellulose, and hydroxypropylmethylcellulose), hyaluronic acid derivatives, pectin, tragacanth, carrageenan, and sodium alginate.

Gels may be easy to manufacture, comfortable, and have the ability to spread onto the surface of mucous and to achieve an intimate contact with vaginal mucosa. Moreover, because of the relatively high water content of gels and their rheological properties, gels may present the further advantage of hydrating and lubricating action, which may be useful in pathological situations characterized by dryness of the vaginal mucosa. The use of mucoadhesive polymers may improve the time of contact with the vaginal mucosa, thereby delaying the loss of the formulation and prolonging the desirable effect. Among gelling agents that may be used for forming gels, mention may be made, for example, of tragacanth, acacia gum, polycarbophil, Carbopol® 974P; sodium carboxymethylcellulose; hydroxyethylcellulose, colloidal silicon dioxide, and carrageenan PDR98-15.

The pharmaceutical compositions disclosed herein may be useful when treating women during or after menopause. However, the methods and compositions disclosed herein are not restricted to women in this age group but may be applied to any person in need of treatment.

The pharmaceutical compositions can include other pharmaceutically acceptable excipients, such as, a buffer (e.g., Tris-HCl, acetate, phosphate) of various pH and ionic strength; an additive such as albumin or gelatin to prevent absorption to surfaces; a protease inhibitor, a permeation enhancer; a solubilizing agent (e.g., glycerol, polyethylene glycerol); an anti-oxidant (e.g., ascorbic acid, sodium metabisulfite, butylated hydroxyanisole); a stabilizer (e.g., hydroxypropyl cellulose, hydroxypropylmethyl cellulose): a viscosity increasing agent (e.g., carbomer, colloidal silicon dioxide, ethyl cellulose, guar gum); a sweetener (e.g. aspartame, citric acid); a preservative (e.g., Thimerosal, benzyl alcohol, parabens); a flow-aid (e.g., colloidal silicon dioxide), a plasticizer (e.g., diethyl phthalate, triethyl citrate); an emulsifier (e.g., carbomer, hydroxypropyl cellulose, sodium lauryl sulfate); a polymer coating (e.g., poloxamers or poloxamines, hypromellose acetate succinate): a coating and film forming agent (e.g., ethyl cellulose, acrylates, polymethacrylates, hypromellose acetate succinate); an adjuvant; a pharmaceutically acceptable carrier for liquid formulations, such as an aqueous (water, alcoholic/aqueous solution, emulsion or suspension, including saline and buffered media) or non-aqueous (e.g., propylene glycol, polyethylene glycol, and injectable organic esters such as ethyl oleate) solution, suspension, emulsion or oil; and a parenteral vehicle (for subcutaneous, intravenous, intraarterial, or intramuscular injection), including but not limited to, sodium chloride solution, Ringer's dextrose, dextrose and sodium chloride, lactated Ringer's and fixed oils.

Intravenous vehicles may include fluid and nutrient replenishers, electrolyte replenishes such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions. Examples of oils are those of animal, vegetable, or synthetic origin, for example, peanut oil, soybean oil, olive oil, sunflower oil, fish-liver oil, another marine oil, or a lipid from milk or eggs.

In certain embodiments, the pharmaceutically acceptability excipient is a non-naturally occurring excipient.

In one embodiment, the solid dispersion comprising ospemifene and a hydrophilic carrier further comprises one or more of the following pharmaceutically acceptable excipients: colloidal silicon dioxide, lactose monohydrate, magnesium stearate, mannitol, microcrystalline cellulose, polyethylene glycol, pre-gelatinized starch, sodium starch glycolate, titanium dioxide, triacetin, and triose. In another embodiment, the solid dispersion comprising ospemifene and a hydrophilic carrier further comprises the following pharmaceutically acceptable excipients: colloidal silicon dioxide, lactose monohydrate, magnesium stearate, mannitol, microcrystalline cellulose, polyethylene glycol, pre-gelatinized starch, sodium starch glycolate, titanium dioxide, triacetin, and triose.

These excipients are provided by way of example and it will be known to those of skill in the art that there will be other or different excipients that can provide the same chemical features as those listed herein.

5. Methods of Making Solid Dispersions

The solid dispersions can be made using any useful method. Melting and solvent evaporation methods are two major processes of preparing solid dispersions. In the melting process, generally, one or more hydrophilic carriers including, but not limited to, povidone, copovidone, HPMC, HPMCAS, Eudragit® compounds, polyvinyl caprolactam-polyvinyl acetate polyethylene glycol graft co-polymers, and HPMCP or mixtures thereof, and an API, such as ospemifene, are combined either with or without a solvent (e.g., one or more of water or a lower alkyl alcohol) to form a mixture (e.g., a liquid mixture) or a solution. Optionally, the hydrophilic carrier and API, either with or without additional pharmaceutically acceptable excipients, can be heated near or past the glass transition temperature $T_g$ or melting temperature $T_m$ to form a liquid mixture or solution. Then, the resulting solution can be spray dried to form a solid dispersion. Alternatively, the method includes a hot-melt extrusion process, where the mixture is heated to form a homogenous molten mass, extruded, and cooled to form a solid dispersion. The extrudates can optionally be pelletized or milled to form a solid dispersion amenable for further processing in a suitable unit dosage form.

Another common method of a preparing a solid dispersion is the solvent evaporation process in which the API and carrier are dissolved in a common organic solvent (e.g., one or more of water or a lower alkyl alcohol) to form a mixture (e.g., a liquid mixture) or a solution followed by removal of the solvent by evaporation at elevated temperature and/or under vacuum.

In making a solid dispersion, it is possible to vary the ratio of drug to hydrophilic carrier in order to optimally affect the performance of the drug. For example, in the case of ospemifene, it is possible to mix ospemifene with a hydrophilic carrier including, but not limited to, povidone, copovidone, HPMC, HPMCAS, Eudragit® compounds, polyvinyl caprolactam-polyvinyl acetate polyethylene glycol graft co-polymers, and HPMCP or mixtures thereof, in a ratio ranging from about 2:1 to 1:50, about 1:1 to about 1:20 (w/w), from about 1:1 to about 1:15 (w/w), from about 1:1 to about 1:10 (w/w), from about 1:1 to about 1:5 (w/w), from about 1:2 to about 1:5, or from about 1:2 to about 1:4 (w/w). In some embodiments, the ratio of ospemifene to hydrophilic carrier is about 1:4 (w/w). In some embodiments, the ratio of ospemifene to hydrophilic carrier in the solid dispersion is selected from the group consisting of about 1:1, about 1:2, about 1:3, about 1:4, about 1:5, about 1:6, about 1:7, about 1:8, about 1:9, about 1:10, about 1:11, about 1:12, about 1:13, about 1:14, about 1:15, about 1:16, about 1:17, about 1:18, about 1:19, and about 1:20 (w/w). In some embodiments, the ratio of ospemifene to hydrophilic carrier in the solid dispersion is about 1:1, about 1:2, about 1:3, about 1:4, about 1:5, about 1:6, about 1:7, about 1:8, about 1:9, about 1:10, about 1:11, about 1:12, about 1:13, about 1:14, about 1:15, about 1:16, about 1:17, about 1:18, about 1:19, or about 1:20 (w/w).

In some embodiments of making the solid dispersion, the hydrophilic carrier is combined with the API, such as ospemifene, and a surfactant, as described herein. In these cases, the amount of surfactant may range from about 1:1 to about 1:10 (surfactant: hydrophilic carrier). In some embodiments, the ratio of surfactant to hydrophilic carrier in the solid dispersion is selected from the group consisting of about 1:1, about 1:2, about 1:3, about 1:4, about 1:5, about 1:6, about 1:7, about 1:8, about 1:9, and about 1:10.

In general, it will also be advantageous to subject the API, such as ospemifene, to one or more micronization methods in order to produce particles of a suitable size for compounding into a solid dispersion dosage form. Methods well known in the art that are suitable for use in the processing of ospemifene for production of solid dispersions include, but are not limited to: solvent evaporation such as film casting, roto-evaporation, spray drying, spray coating, freeze drying, vacuum drying, supercritical fluid precipitation, anti-solvent precipitation, controlled micro-crystallization, hot melt extrusion, injection molding, melting (fusion) method, melt agglomeration, and co-grinding.

For example, a melt-extrusion process can comprise the steps of preparing a melt that includes the active ingredient(s), the carrier(s) and optionally additional excipients, and cooling the melt until it solidifies. In many cases, a hydrophilic carrier will melt and the other components including the API, such as ospemifene, and other added excipients will dissolve in the melt thereby forming a substantially homogenous dispersion. The preparation of the melt can take place in a variety of ways. The mixing of the components can take place before, during or after the formation of the melt. For example, the components can be mixed first and then melted or be simultaneously mixed and melted. The melt can also be homogenized in order to disperse the API, such as ospemifene, efficiently. In addition, it may be convenient first to melt the carriers) and then to mix in and homogenize the active ingredient(s).

Spray drying involves breaking up liquid mixtures into small droplets and rapidly removing solvent from the mixture in a container (spray drying apparatus) that provides a strong driving force inducing evaporation of solvent from the droplets. This is often provided by maintaining the partial pressure of solvent in the spray drying apparatus, well below the vapor pressure of the solvent at the temperatures of the drying droplets, and or providing heat. This may be accomplished by either (1) maintaining the pressure in the spray drying apparatus at a partial vacuum; (2) mixing the liquid droplets with a warm drying gas, for example heated nitrogen gas; or (3) both. Spray drying apparatus suitable for the present invention can be any of the various commercially available apparatus. Non-limiting examples of specific spray drying devices include those manufactured by Niro Inc., Buchi Labortechnik AG, and Spray Drying Systems, Inc.

Besides melt extrusion and spray drying and other solid dispersion technologies, the pre-tableting material can also be prepared using other methods, such as wet granulation, dry granulation or fluidized bed granulation. All ingredients in the pre-tabletting material preferably are well granulated and mixed, such that the tablet formed from these materials comprises a substantially even distribution of the API, such as ospemifene, and the amount of the API in each tablet is about equal.

In some embodiments, a solid dispersion of ospemifene and a hydrophilic carrier can be made by first dissolving ospemifene and the carrier separately in suitable solvents. In certain embodiments, the ospemifene and carrier (and optionally surfactant) are dissolved in the same solvent. In some cases, the solvent can be water. In other cases a lower alkyl alcohol, for example methanol or ethanol, can be used. The ospemifene and hydrophilic carrier (and optionally surfactant) solutions can then be mixed together to produce a drug/carrier admixture. This admixture is then poured into a suitable vessel and the solvent(s) allowed to evaporate, a method generally referred to as a solvent casting method. Although it is desirable to remove as much solvent as possible, certain small amounts of residual solvent typically remain in the solid dispersion formed by these methods. In some cases, evaporation can be performed under ambient conditions of temperature and atmospheric pressure, for example in a fume hood. In other cases, it may be desirable to accelerate solvent evaporation by heating, reducing atmospheric pressure, or a combination of heat and reduced pressure.

Solvent evaporation leaves behind a solid dispersion, which in some cases will form a thin film in the vessel in which evaporation was performed. This thin film can then be further processed, for example by pulverization, to produce a fine powder form of the solid dispersion. This powder is then suitable for further pharmacological or chemical testing, or compounding into a solid dosage form. In some cases, a solid dosage form can comprise additional pharmaceutically acceptable excipients in order to improve the physiological performance of the ospemifene in a solid dispersion dosage form.

The solid dispersion can be blended with one or more pharmaceutically acceptable excipients, as described herein, and then milled, blended, granulated and/or compacted to produce a final blend for encapsulating or tabletting. In particular embodiments, the one or more pharmaceutically acceptable excipients include a binder, a surfactant, a filler, a disintegrant, a wetting agent, a glidant, and a lubricant.

6. Dosage and Administration

A pharmaceutical composition as disclosed herein is formulated to be compatible with its intended route of administration. Methods to accomplish the administration are known to those of ordinary skill in the art. This includes, for example, injections, by parenteral routes such as intravenous, intravuscular, intraarterial, subcutaneous, intramuscular, intraperitoneal, intraventricular, intraepidural, or others as well as oral, nasal, ophthalmic, rectal, or topical. Sustained release administration is also specifically contemplated, by such means as depot injections or credible implants. Localized delivery is also contemplated, by such means as delivery via a catheter to one or more arteries, such as the renal artery or a vessel supplying a localized site of interest. In one embodiment, the solid dispersion form is formulated to be administered orally.

The currently recommended daily dosage for ospemifene in the treatment of symptoms related to menopause is 60 mg daily by oral administration. Pharmacokinetic studies have examined the distribution of ospemifene in the body, as well as routes of elimination, following oral administration of a 60 mg dose (Koskimies et al., 2013). The results of these studies demonstrated that of the total dose administered, 75% is eliminated via the fecal route. This means that following oral administration of other previous dosage forms of ospemifene, the majority of the drug never becomes soluble and/or absorbed, and therefore never reaches its biological target. Thus, with certain previous forms of oral ospemifene, most of the drug simply passes through the body without exerting any therapeutic benefit.

With the significantly enhanced solubility provided by the solid dispersions as described, it will now be possible to provide a lower daily dosage of ospemifene and still achieve pharmaceutically effective levels of the drug. So, for example, instead of requiring 60 mg per day, a therapeutically effective dose may consist of significantly less ospemifene, and yet still achieve comparable circulating levels of the drug.

In some embodiments, an effective dosage of an ospemifene solid dispersion comprises 60 mg ospemifene per day. In another embodiment, an effective dosage of ospemifene comprises less than 50 mg per day. In another embodiment, an effective dosage of ospemifene comprises less than 40 mg per day. In yet another embodiment, an effective dosage of ospemifene comprises less than 30 mg per day. In yet another embodiment, an effective dosage of ospemifene comprises less than 25 mg per day. In yet another embodiment, an effective dosage of ospemifene comprises less than 20 mg per day. In yet another embodiment, an effective dosage of ospemifene comprises less than 17.5 mg per day. In yet another embodiment, an effective dosage of ospemifene comprises less than 15 mg per day. In yet another embodiment, an effective dosage of ospemifene comprises less than 12.5 mg per day. In yet another embodiment, an effective dosage of ospemifene comprises less than 10 mg per day. In yet another embodiment, an effective dosage of ospemifene comprises less than 7.5 mg per day. In yet another embodiment, an effective dosage of ospemifene comprises less than 5 mg per day. In yet another embodiment, an effective dosage of ospemifene comprises less than 2.5 mg per day. In yet another embodiment, an effective dosage of ospemifene comprises less than 1 mg per day.

In certain embodiments, an effective dosage of ospemifene comprises about 5-50 mg per day, 5-45 mg per day, 5-40 mg per day, 5-35 mg per day, 5-30 mg per day, 5-25 mg per day, 5-20 mg per day, 5-15 mg per day, 5-10 mg per day, 10-50 mg per day, 10-45 mg per day, 10-40 mg per day, 10-35 mg per day, 10-30 mg per day, 10-25 mg per day, 10-20 mg per day, 10-15 mg per day, 15-50 mg per day, 15-45 mg per day, 15-40 mg per day, 15-35 mg per day, 15-30 mg per day, 15-25 mg per day, 15-20 mg per day, 20-50 mg per day, 20-45 mg per day, 20-40 mg per day, 20-35 mg per day, 20-30 mg per day, 20-25 mg per day, 25-50 mg per day, 25-45 mg per day, 25-40 mg per day, 25-35 mg per day, 25-30 mg per day, 30-50 mg per day, 30-45 mg per day, 30-40 mg per day, 30-35 mg per day, 35-50 mg per day, 35-45 mg per day, 35-40 mg per day, 40-50 mg per day, 45-50 mg per day, or about 50 mg per day.

In yet another embodiment, an effective dosage of ospemifene comprises about 1, about 2, about 3, about 4, about 5, about 6, about 7, about 8, about 9, about 10, about 11, about 12, about 13, about 14, about 15, about 16, about 17, about 18, about 19, about 20, about 25, about 30, about 35, about 40, about 45, about 50, or about 55 mg per day.

Ospemifene has beneficial effects on total cholesterol as well as HDL and LDL cholesterol levels, as well as preventing osteoporosis and early stage breast cancer. Ospemifene is also useful in the treatment of desire disorders, arousal disorders, orgasmic disorders and dyspareunia in post-menopausal women. Dyspareunia is a condition characterized by pain during intercourse, and is typically a symptom of vulvar and vaginal atrophy that occurs concomitant with menopause. By providing a solid dosage form with significantly improved solubility, it may be possible to use dosages comparable to or less than the currently recommended daily dose, and yet achieve similar or better physiological outcomes in patients for whom ospemifene is indicated.

7. Method of Treatment

Ospemifene, as discussed, has a number of beneficial effects in relieving symptoms related to menopause including, but not limited to, various symptoms of female sexual dysfunction, including, but not limited to, desire disorders, arousal disorders, orgasmic disorders, vaginal dryness, and painful intercourse (dyspareunia). Most of these symptoms are the result of the changes in hormone status that accompanies menopause, especially reduced levels of estrogen and testosterone. Thus, the solid dispersion forms of ospemifene and a hydrophilic carrier are useful in methods of treating such symptoms.

In addition to the various disorders of sexual function that are associated with menopause, reduced levels of estrogen in females have been linked to bone loss leading to osteoporosis. Nearly 80% of Americas with osteoporosis are female, and half of women over the age of 50 will suffer a bone fracture related to osteoporosis. Osteoporosis is also common in older men. Ospemifene, being a selective estrogen receptor modulator (SERM), is able to bind the estrogen receptor ($E_R$) and confer $E_R$ agonist or antagonist effects depending on the target tissue. Thus, given its ability to ameliorate the loss of estrogen production following menopause, ospemifene can be used in tire treatment of osteoporosis. Indeed, ospemifene has been shown to increase bone mineral density in men with prostate cancer who were treated with gonadotropin-releasing agonists. Smith, Matthew, Rev. Urol. 7 (Suppl 3):S30-S35 (2005). Thus, the solid dispersion forms of ospemifene and a hydrophilic carrier are also useful in methods of treating osteoporosis.

The solid dispersion dosage form will provide ospemifene, in an amount effective to provide relief from these symptoms and/or conditions. In addition, the solid dispersion dosage form will be able to provide circulating ospemifene levels comparable to those obtained with previous dosage forms comprising 60 mg of ospemifene, yet will use less than the currently recommended daily dosage of 60 mg of ospemifene. Thus, in one embodiment, ospemifene is administered at a dosage less than 60 mg per day. In another embodiment, ospemifene is administered at a dosage less than 50 mg per day. In another embodiment, ospemifene is administered at a dosage less than 40 mg per day. In yet another embodiment, ospemifene is administered at a dosage less than 30 mg per day. In yet another embodiment, ospemifene is administered at a dosage of less than 25 mg per day. In yet another embodiment, ospemifene is administered at a dosage of less than 20 mg per day. In yet another embodiment, ospemifene is administered at a dosage of less than 173 mg per day. In yet another embodiment, ospemifene is administered at a dosage of less than 15 mg per day. In yet another embodiment, ospemifene is administered at a dosage of less than 12.5 mg per day. In yet another embodiment, ospemifene is administered at a dosage of less than 10 mg per day. In yet another embodiment, ospemifene is administered at a dosage of less than 7.5 mg per day. In yet another embodiment, ospemifene is administered at a dosage of less than 5 mg per day. In yet another embodiment, ospemifene is administered at a dosage of less than 2.5 mg per day. In yet another embodiment, ospemifene is administered at a dosage of less than 1 mg per day. In certain embodiments, ospemifene is administered at a dosage of about 5-50 mg per day, 5-45 mg per day, 5-40 mg per day, 5-35 mg per day, 5-30 mg per day, 5-25 mg per day, 5-20 mg per day, 5-15 mg per day, 5-10 mg per day, 10-50 mg per day, 10-45 mg per day, 10-40 mg per day, 10-35 mg per day, 10-30 mg per day, 10-25 mg per day, 10-20 mg per day, 10-15 mg per day, 15-50 mg per day, 15-45 mg per day, 15-40 mg per day, 15-35 mg per day, 15-30 mg per day, 15-25 mg per day, 15-20 mg per day, 20-50 mg per day, 20-45 rag per day, 20-40 mg per day, 20-35 mg per day, 20-30 mg per day, 20-25 mg per day, 25-50 mg per day, 25-45 mg per day, 25-40 mg per day. 25-35 mg per day, 25-30 mg per day, 30-50 mg per day, 30-45 mg per day, 30-40 mg per day, 30-35 mg per day, 35-50 mg per day, 35-45 mg per day, 35-40 mg per day, 40-50 mg per day, 45-50 mg per day, or about 50 mg per day.

One aspect is directed to methods of treating a symptom related to menopause, the method comprising administering a solid dispersion dosage form of ospemifene and a hydrophilic carrier, including, but not limited to, povidone, copovidone, HPMC, HPMCAS, Eudragit® compounds, polyvinyl caprolactam-polyvinyl acetate polyethylene glycol graft co-polymers, and HPMCP or mixtures thereof, and optionally a surfactant to a patient in an amount sufficient to treat symptoms related to menopause, including, but not limited to, various symptoms of female sexual dysfunction, such as, desire disorders, arousal disorders, orgasmic disorders, vaginal dryness and painful intercourse (dyspareunia).

Another aspect is directed to a method of treating osteoporosis, the method comprises administering a solid dispersion dosage form of ospemifene and a hydrophilic carrier including, but not limited to, povidone, copovidone, HPMC, HPMCAS, Eudragit® compounds, polyvinyl caprolactam-polyvinyl acetate polyethylene glycol graft co-polymers, and HPMCP or mixtures thereof, and optionally a surfactant to a patient in an amount sufficient to treat osteoporosis.

Another aspect Is directed to a solid dispersion dosage form comprising ospemifene and a hydrophilic carrier including, but not limited to, povidone, copovidone, HPMC, HPMCAS, Eudragit® compounds, polyvinyl caprolactam-polyvinyl acetate polyethylene glycol graft co-polymers, and HPMCP or mixtures thereof, and optionally a surfactant for use in treating symptoms related to menopause, including, but not limited to, various symptoms of female sexual dysfunction, such as, desire disorders, arousal disorders, orgasmic disorders, vaginal dryness, and painful intercourse (dyspareunia). Another aspect is directed to a solid dispersion dosage form comprising ospemifene and a hydrophilic carrier including, but not limited to, povidone, copovidone, HPMC, HPMCAS, Eudragit® compounds, polyvinyl caprolactam-polyvinyl acetate polyethylene glycol graft co-polymers, and HPMCP or mixtures thereof, and optionally a surfactant for use in treating osteoporosis.

One embodiment is directed to a solid dispersion dosage form comprising ospemifene and HPMCAS, and optionally a surfactant, for use in treating symptoms related to menopause, including, but not limited to, various symptoms of female sexual dysfunction, such as, desire disorders, arousal disorders, orgasmic disorders, vaginal dryness, and painful intercourse (dyspareunia). Another embodiment is directed to a solid dispersion dosage form comprising ospemifene and HPMCAS, and optionally a surfactant, for use in treating osteoporosis.

Another embodiment is directed to a solid dispersion dosage form comprising ospemifene and HPMC, and optionally a surfactant, for use in treating symptoms related to menopause, including, but not limited to, various symptoms of female sexual dysfunction, such as, desire disorders, arousal disorders, orgasmic disorders, vaginal dryness, and painful intercourse (dyspareunia). Another embodiment is directed to a solid dispersion dosage form comprising ospemifene and HPMC, and optionally a surfactant, for use in treating osteoporosis.

Another embodiment is directed to a solid dispersion dosage form comprising ospemifene and copovidone, and optionally a surfactant, for use in treating symptoms related to menopause, including, but not limited to, various symptoms of female sexual dysfunction, such as, desire disorders, arousal disorders, orgasmic disorders, vaginal dryness, and painful intercourse (dyspareunia). Yet another embodiment, is directed to a solid dispersion dosage form comprising ospemifene and copovidone, and optionally a surfactant, for use in treating osteoporosis.

Another embodiment is directed to a solid dispersion dosage form comprising ospemifene and povidone, and optionally a surfactant, for use in treating symptoms related to menopause, including, but not limited to, various symptoms of female sexual dysfunction, such as, desire disorders, arousal disorders, orgasmic disorders, vaginal dryness, and painful intercourse (dyspareunia). Yet another embodiment, is directed to a solid dispersion dosage form comprising ospemifene and povidone, and optionally a surfactant, for use in treating osteoporosis.

Still another embodiment is directed to a solid dispersion dosage form comprising ospemifene and a polyvinyl caprolactam-polyvinyl acetate polyethylene glycol graft co-polymer (e.g., Soluplus®), and optionally a surfactant, for use in treating symptoms related to menopause, including, but not limited to, various symptoms of female sexual dysfunction, such as, desire disorders, arousal disorders, orgasmic disorders, vaginal dryness, and painful intercourse (dyspareunia). Yet another embodiment, is directed to a solid dispersion dosage form comprising ospemifene and a polyvinyl caprolactam-polyvinyl acetate polyethylene glycol graft co-polymers (e.g., Soluplus®), and optionally a surfactant, for use in treating osteoporosis.

Still another embodiment is directed to a solid dispersion dosage form comprising ospemifene and hydroxypropylcellulose (e.g., HPC-SSL) and optionally a surfactant, for use in treating symptoms related to menopause, including, but not limited to, various symptoms of female sexual dysfunction, such as, desire disorders, arousal disorders, orgasmic disorders, vaginal dryness, and painful intercourse (dyspareunia). Yet another embodiment, is directed to a solid dispersion dosage form comprising ospemifene and hydroxypropylcellulose (e.g., HPC-SSL), and optionally a surfactant, for use in treating osteoporosis.

Still another embodiment is directed to a solid dispersion dosage form comprising ospemifene and hydroxypropyl methylcellulose phthalate (HPMCP) (e.g., HP-55), and optionally a surfactant, for use in treating symptoms related to menopause, including, but not limited to, various symptoms of female sexual dysfunction, such as, desire disorders, arousal disorders, orgasmic disorders, vaginal dryness, and painful intercourse (dyspareunia). Yet another embodiment, is directed to a solid dispersion dosage form comprising ospemifene and hydroxypropyl methylcellulose phthalate (HPMCP) (e.g., HP-55), and optionally a surfactant, for use in treating osteoporosis.

Still another embodiment is directed to a solid dispersion dosage form comprising ospemifene and a Eudragit® compound (e.g., Eudragit® L100-55), and optionally a surfactant, for use in treating symptoms related to menopause, including, but not limited to, various symptoms of female sexual dysfunction, such as, desire disorders, arousal disorders, orgasmic disorders, vaginal dryness, and painful intercourse (dyspareunia). Yet another embodiment, is directed to a solid dispersion dosage form comprising ospemifene and a Eudragit® compound (e.g., Eudragit® L100-55), and optionally a surfactant, for use in treating osteoporosis.

In certain embodiments, the ospemifene solid dispersion dosage forms are administered in a fasted state or without food. In certain embodiments, after a single administration in a human subject of the ospemifene solid dispersion dosage form there is greater bioavailability or no substantial difference in the bioavailability of ospemifene when the formulation is administered to the subject in a fasted versus a fed state. In other words, in certain embodiments, food does not increase the bioavailability of the ospemifene solid dispersion dosage form, as it docs with other ospemifene formulations, such as Osphena®, where solubility is significantly better in the fed state.

Given the improved solubility of certain solid dispersions as described herein, it is expected that one dosage form could comprises a dosage form in which a powder is added to a buffered solution that the individual could then consume like a regular beverage. Given the improved solubility, it is now possible to orally deliver ospemifene at therapeutically effective doses in volume that could be administered in a single serving. This may provide additional advantage for people who have difficulty in taking pills, tablets and other normal oral dosage forms of medications.

EXAMPLES

The examples provided above are simply for illustrative purposes. Those of skill in the art will be able to readily determine appropriate methods and equipment in order to produce suitable solid dispersion forms as described herein.

Example 1: Solubility Studies of Ospemifene Solid Dispersions with HMPCAS, HMPC, Povidone, and Copovidone Ospemifene is a BCS class II compound with poor water solubility and high permeability. Ospemifene has a solubility of less than about 0.3 μg/mL in water or buffered solutions over the pH range from about 1.2 to about 8.0. Ospemifene is normally produced in a highly crystalline form with melting point in the range of about 115° C. to about 127° C. It is generally recognized that the amorphous form remains in a higher energy state than its crystalline counterparts and in turn shows enhanced solubility. However, amorphous ospemifene is challenging to produce.

In the studies disclosed herein, solid dispersions of ospemifene in combination with hydrophilic carriers including hydroxyl propyl methyl cellulose (HPMC), povidone (PVP), copovidone, and hypromellose acetate succinate (HPMCAS) were prepared, and their relative solubility as compared to ospemifene alone were determined.

Materials

Materials used in the studies disclosed herein, including the API, hydrophilic carriers and solvents are set out in Table I.

TABLE I

List of Materials Used

| Item Number | Material | Vendor |
|---|---|---|
| 1 | Ospemifene | Fermion |
| 2 | Kollidon ® 30 (PVP) | BASF |
| 3 | Kollidon ® VA64 (co-povidone) | BASF |
| 4 | Pharmacoat ® 615 (HPMC) | Shin-Etsu |
| 5 | HPMCAS AQOAT LF | Shin-Etsu |
| 6 | Ethanol | Acros |
| 7 | Methanol | Fisher Scientific |

Method of Preparing of Solid Dispersions Comprising Ospemifene

Solid dispersions of ospemifene with a hydrophilic carrier including PVP, copovidone, HPMC, or HPMCAS, were prepared using a solvent casting method.

In each preparation, 1 g of ospemifene and a hydrophilic carrier were dissolved in a common solvent at a ratio ranging from about 1:1 w/w to about 1:20 w/w, and particularly in a ratio of about 1:4 w/w. The solution mixtures of ospemifene and the particular hydrophilic carrier being evaluated were then poured into petri dishes and then dried by evaporation in a fume hood for approximately 48 hours. The resulting thin film solid dispersions were then recovered from the petri dishes and pulverized using a mortar and pestle.

In developing methods of evaluating the solubility of the various compositions produced in these studies, a common solvent was selected that was capable of dissolving both ospemifene and each of the hydrophilic carriers being evaluated. Based on previous studies, it was known that ospemifene is not soluble in water, but is soluble in ethanol, propanol, and acetonitrile. Thus, an incremental solvent addition method was used to estimate the solubility in methanol and ethanol co-solvent mixture.

The solubility of ospemifene is about 67 mg/mL in methanol, and about 57 mg mL in ethanol. Based on the solubility data of ospemifene and hydrophilic carriers, ethanol was selected for use in preparing solutions of API with PVP or copovidone, respectively. As summarized in Table II, an ethanol/water mixture was used for preparing API and HPMC mixtures. Methanol alone was used as the solvent for preparing solutions of API and HPMCAS. In some cases, 0.2 g of ospemifene and 0.8 g of carrier were dissolved separately in a suitable solvent, and then mixed together to form a mixed solution. In order to produce a dried cast film of each ospemifene/carrier formulation, the mixed solution was poured into a petri dish and allowed to dry by evaporation in a fume hood at room temperature over a period of about 48 hours.

TABLE II

Preparation of Ospemifene API and Carrier Solutions

| Sample | Ospemifene (g) | Carrier (g) | Solvent for API | Solvent for carrier | Solvent total |
|---|---|---|---|---|---|
| OSP/PYP | 0.20 | 0.80 | 3.5 mL Ethanol | 6.5 mL Ethanol | 10.0 mL Ethanol |
| OSP/Co-povidone | 0.20 | 0.80 | 3.5 mL Ethanol | 6.5 mL Ethanol | 10.0 mL Ethanol |
| OSP/HPMC | 0.20 | 0.80 | 3.5 mL Ethanol | 3.0 mL water, 13.5 mL Ethanol | 20.0 mL Ethanol/Water (85:15 (v/v)) |
| OSP/HPMCAS | 0.20 | 0.80 | 3.0 mL Methanol | 17.0 mL Methanol | 20.0 mL Methanol |

It is also contemplated that variations can be made to these methods while still providing solid dispersion forms of ospemifene with enhanced solubility. For example, it is expected that rather than passive drying in a fume hood, drying under reduced pressure would be effective to more rapidly remove solvent when making the thin films for eventual processing into powders or other forms. Similarly, methods for producing sufficiently fine particles suitable for compounding into a final dosage form; for example, an oral dosage form such as a tablet, capsule, or powder might involve techniques other than pulverizing solid dispersion films in a mortar and pestle. Techniques such as jet milling, ball milling or other types of micronization methods will be applicable to processing the solid dispersion forms described.

Following evaporation, each of the thin films was recovered using a spatula and transferred to a mortar and pestle for grinding. Conveniently, it was discovered that the solid dispersions comprising ospemifene and PVP, copovidone, or HPMCAS could be ground into fine powders. However, the solid dispersion including HPMC was observed to adhere strongly to surfaces, and was therefore difficult to pulverize into a fine powder. The yields obtained of each formulation are shown in Table III.

TABLE III

Yield of Ospemifene Solid Dispersions

| Solid dispersion | Ratio | Starting weight (g) | Final weight (g) | Yield |
|---|---|---|---|---|
| OSP/PVP | 1:4 (w/w) | 1.0 | 0.65 | 65% |
| OSP/Co-povidone | 1:4 (w/w) | 1.0 | 0.28 | 28% |
| OSP/HPMC | 1:4 (w/w) | 1.0 | 0.94 | 94% |
| OSP/HPMCAS | 1:4 (w/w) | 1.0 | 0.33 | 33% |

The foregoing is an example of one method of preparation of combining ospemifene with a hydrophilic carrier in solution, and then producing a dried solid dispersion of ospemifene and the carrier. Those of skill in the art will recognize that the order of steps in some cases will be based on preference and are not strictly limiting. In addition, the scale of preparation can be varied depending on preference and is not meant to imply that the solid dispersions can only be prepared in the amounts provided in the example. Similarly, other solvents other than those used in the specific example provided herein may be compatible with method of producing solid dispersion of ospemifene. Thus, the exemplary method of preparing these solid dispersions is for illustrative purposes only and is not meant to be limiting to the scope of the inventive concept.

Method of Preparing Physical Mixtures Comprising Ospemifene

As controls, simple physical mixtures of ospemifene and a hydrophilic carrier (PVP, copovidone, HPMC, or HPMCAS) in a range from about 1:1 to about 1:20 (w/w), and in particular a ratio of about 1:4 (w/w), were prepared by manually tumbling ospemifene with the hydrophilic carrier of interest.

Solubility Measurements

Solubility measurements of the solid dispersions and physical mixtures were performed using a shake flask method. Individual test samples comprising about 5 mg ospemifene, 30 mg of each physical mixture, or 30 mg of each solid dispersion, were mixed with 20 mL of an aqueous media (either water alone, 0.1N HCl, or a buffered aqueous solution comprising 50 mM phosphate, pH 6.8). The sample was agitated manually for 3 hours. Following mixing, a 1.5 mL sample was withdrawn to a micro-centrifuge tube and centrifuged at 12,000 rpm for 10 min. About 1 mL of supernatant was then transferred to a HPLC vial for HPLC analysis.

HPLC Analysis

The conditions used in the HPLC method are set forth in Table IV.

TABLE IV

| HPLC method for assaying ospemifene | |
|---|---|
| Column | Waters Symmetry C18, 4.6 × 150 mm, 3.5 μm |
| Column temperature | 30° C. |
| Wavelength | 235 nm |
| Flow rate | 1.4 mL/min |
| Injection volume | 20 μL |
| Mobile phase A | Acetonitrile |
| Mobile phase B | THF/Acetonitrile/Water 40/200/800 v/v/v |
| Isocratic | 47% A, 53% B |
| Run time | 15 min |

Results

Solubility of Ospemifene Solid Dispersion Formulations

The solubilities of ospemifene solid dispersions, the control physical mixtures, and ospemifene alone were determined by HPLC in water, 0.1 N HCl, or 50 mM pH 6.8 buffer using a shake flask method, as described above. The solubility data are presented in Table V.

TABLE V

Solubility Results

| | Solubility (μg/mL) | | |
|---|---|---|---|
| | Water | 0.1N HCl | 50 mM PO$_4$, pH 6.8 |
| Ospemifene Alone | | | |
| Ospemifene (OSP) | 0.04 | <0.03 | <0.03 |
| Ospemifene/PVP | | | |
| Physical Mixture (PM) | 0.30 | <0.03 | <0.03 |
| Solid Dispersion (SD) | 2.76 | 0.42 | 0.06 |
| Solubility Enhancement: Ratio of SD/PM | 9x | 14x | 2x |
| Solubility Enhancement: Ratio of SD/API alone | 69x | 14x | 2x |

TABLE V-continued

Solubility Results

| | Solubility (μg/mL) | | |
|---|---|---|---|
| | Water | 0.1N HCl | 50 mM PO$_4$, pH 6.8 |
| Ospemifene/Copovidone | | | |
| Physical Mixture (PM) | 0.25 | 0.12 | 0.03 |
| Solid Dispersion (SD) | 3.31 | 3.36 | 2.10 |
| Solubility Enhancement: Ratio of SD/PM | 13x | 28x | 70x |
| Solubility Enhancement: Ratio of SD/API alone | 83x | 112x | 70x |
| Ospemifene/HPMC | | | |
| Physical Mixture (PM) | 0.03 | <0.03 | 0.03 |
| Solid Dispersion (SD) | 2.02 | 0.57 | 1.59 |
| Solubility Enhancement: Ratio of SD/PM | 67x | 19x | 53x |
| Solubility Enhancement: Ratio of SD/API alone | 51x | 19x | 53x |
| Ospemifene/HPMCAS | | | |
| Physical Mixture (PM) | 0.06 | <0.03 | 0.35 |
| Solid Dispersion (SD)) | 0.24 | 0.10 | 23.28 |
| Solubility Enhancement: Ratio of SD/PM | 4x | 3x | 66x |
| Solubility Enhancement: Ratio of SD/API alone | 6x | 3x | 776x |

Solubility enhancement in the ospemifene/hydrophilic carrier solid dispersions was observed to varying extents in each of the three aqueous media tested. In general, the increase in solubility observed for solid dispersion forms as compared to the respective physical mixture tested in the same aqueous medium ranged from about 2- to about 70-fold. The solid dispersion of ospemifene and HPMCAS dissolved in 50 mM PO$_4$, pH 6.8 exhibited an unexpected 776-fold increase in solubility as compared the corresponding physical mixture. The solubility values measured for physical mixtures of ospemifene and copovidone were comparable to that of ospemifene alone, suggesting good physical stability.

The solubility of solid dispersions comprising ospemifene+HPMCAS exhibited a pH dependence. Solubility in water and 0.1 N HCl were 0.24 μg/mL and 0.10 μg/mL, respectively, while in buffered phosphate solution solubility was 23.28 μg/mL, a surprising increase of nearly 800-fold as compared to ospemifene alone. Also surprising was the observation that ospemifene maintained these high, supersaturated levels even after 3 hours at room temperature.

In addition, as shown in Table V, solid dispersions comprising ospemifene and copovidone unexpectedly showed significantly enhanced solubility in all three solvents tested. More specifically, using a solid dispersion comprising ospemifene and copovidone, solubility was enhanced from more than 80-fold in water, 70-fold in 50 mM phosphate, pH 6.8, and more than 100-fold in 0.1N HCl.

The solubility of solid dispersions comprising ospemifene and povidone unexpectedly increased 69-fold in water, while the solubility of solid dispersions comprising ospemifene and HPMC unexpectedly increased 67-fold in water and 53-fold in 50 mM PO$_4$ buffer, pH 6.8.

Although it has been previously reported that the presence of a hydrophilic carrier in a solid dispersion can enhance the solubility of a drug, it is difficult to predict the degree of solubility enhancement that can be achieved, likely because the proportion in each formulation will be unique depending on the API and the carrier used to produce any particular solid dispersion form. Even so, previously published data have suggested solubility enhancement on the order of 10-fold as typical, with 50 to 100-fold being rarely reported.

For example, U.S. Patent Publication No. 2013/012335 (the entirety of which is incorporated by reference herein) discloses solid dispersion forms of dronedarone where an enhancement of 2- to 13-fold was achieved in a buttered solution at pH 6.8. Similarly, others have reported the evaluation of various carriers as carriers in solid dispersion forms of nifedipine (Tanno et al., 2012). The maximum enhancement in solubility achieved in those studies was 4-fold in a buffer solution at pH 6.8.

Other studies have compared the effect of various carriers in solid dispersions with respect to solubility enhancement. For example, studies comparing the effects of HPMCAS or PVP on the solubility of indomethacin indicated that HPMCAS performed better than PVP, although the maximum enhancement observed was only 9-fold (Sun et al., 2012). In other studies examining forty-one poorly soluble compounds, HPMCAS was found to be the most effective at maintaining drug super-saturation. However, the best performance with respect to solubility enhancement was at best 50- to 80-fold as compared to the API alone, and for most compounds solubility enhancement ranged from about 2- to 20-fold (Curatolo et al., 2009).

Thus, the ospemifene solid dispersions made using copovidone, HPMCAS, povidone, or HPMC showed surprising solubility and stability properties and as such provide significant advantages over current dosage forms of ospemifene.

Example 2: Solubility Studies of Ospemifene Solid Dispersions with Other Hydrophilic Carriers Solid dispersions comprising ospemifene and a hydrophilic carrier selected from Eudragit L100, hydroxypropylcellulose (HPC), Poloxamer 407, Soluplus®, and hydroxypropylmethylcellulose phthalate (HPMCP) were synthesized using the solvent evaporation method as described above in Example 1. The solubility of these ospemifene solid dispersions was analyzed in three aqueous media (water, 0.1 N HCl, or a buffered aqueous solution comprising 50 mM phosphate, pH 6.8) as described above in Example 1.

The results of the solubility assays are provided in Table VI below. The ospemifene solid dispersions synthesized with these other hydrophilic carriers showed enhanced solubility in each of the aqueous media tested. The solubility of solid dispersions comprising ospemifene and Eudragit® L100 unexpectedly increased 83-fold in 50 mM PO$_4$ buffer, pH 6.8, while the solubility of solid dispersions comprising ospemifene and HPC unexpectedly increased 160-fold in water and 240-fold in 0.1N HCl. The solubility of solid dispersions comprising ospemifene and Poloxamer 407 showed marked enhancement of solubility across all three aqueous solutions, including a remarkable 353-fold increase in 50 mM PO$_4$ buffer, pH 6.8. The solubility of solid dispersions comprising ospemifene and Soluplus® showed an unexpected increase of 110-fold in water and 367-fold in 50 mM PO$_4$ buffer, pH 6.8. For solid dispersions comprising ospemifene and HPMCP, the solubility increased 450-fold in 50 mM PO$_4$ buffer, pH 6.8.

TABLE VI

Solubility Results of Solid Dipersions with Other Carriers

| | Solubility (µg/mL) | | |
|---|---|---|---|
| | Water | 0.1N HCl | 50 mM PO$_4$, pH 6.8 |
| Ospemifene/Eudragit ® L100 (1:4) | | | |
| Physical Mixture (PM) | 1.9 | ND | ND |
| Solid Dispersion (SD)) | 0.3 | 0.3 | 2.5 |
| Solubility Enhancement: Ratio of SD/PM | ND | ND | ND |
| Solubility Enhancement: Ratio of SD/API alone | 8x | 10x | 83x |
| Ospemifene/HPC (1:4) | | | |
| Physical Mixture (PM) | ND | ND | ND |
| Solid Dispersion (SD)) | 6.4 | 7.2 | 0.7 |
| Solubility Enhancement: Ratio of SD/PM | ND | ND | ND |
| Solubility Enhancement: Ratio of SD/API alone | 160x | 240x | 23x |
| Ospemifene/Poloxamer 407 (1:4) | | | |
| Physical Mixture (PM) | ND | ND | ND |
| Solid Dispersion (SD)) | 1.1 | 2.0 | 10.6 |
| Solubility Enhancement: Ratio of SD/PM | ND | ND | ND |
| Solubility Enhancement: Ratio of SD/API alone | 28x | 67x | 353x |
| Ospemifene/Soluplus ® (1:4) | | | |
| Physical Mixture (PM) | ND | ND | ND |
| Solid Dispersion (SD)) | 4.4 | 0.6 | 11.0 |
| Solubility Enhancement: Ratio of SD/PM | ND | ND | ND |
| Solubility Enhancement: Ratio of SD/API alone | 110x | 20x | 367x |
| Ospemifene/HPMCP (1:4) | | | |
| Physical Mixture (PM) | ND | ND | 1.4 |
| Solid Dispersion (SD)) | 0.3 | ND | 13.5 |
| Solubility Enhancement: Ratio of SD/PM | ND | ND | 10x |
| Solubility Enhancement: Ratio of SD/API alone | 8x | ND | 450x |

In Table VI, "ND" means "not determined."

Thus, as with the other hydrophilic carriers, the ospemifene solid dispersions made using Soluplus®, Eudragit®L 100-55, Poloxamer 407, HPMCP, and HPC also showed surprising solubility and stability properties and as such provide significant advantages over current dosage forms of ospemifene.

Example 3: Solubility Studies of Ospemifene Solid Dispersions with Hydrophilic Carrier and Surfactant To investigate how surfactants affect the solubility of ospemifene solid dispersion, solid dispersions comprising ospemifene, a hydrophilic carrier (copovidone or povidone), and a surfactant were synthesized using the solvent evaporation method as described above in Example 1. The solubility of these ospemifene solid dispersions was analyzed in three aqueous media (water, 0.1N HCl, or a buffered aqueous solution comprising 50 mM phosphate, pH 6.8) as described above in Example 1.

The results of the solubility assays are provided in the Table VII below. Surfactants, such as Poloxamer 407, sodium docusate, Span® 20, Span® 80, Tween® 80, and Cremophor® EL, increased the solubility of ospemifene to varying degrees, and in several instances, increasing solubility up to several hundred fold as compared to solid dispersions without the surfactant. For example, a solid dispersion comprising ospemifene, copovidone, and Tween 80 had increased solubility of 773×, 610×, and 460× in water, 0.1 N HCl, and 50 mM PO$_4$, pH 6.8, respectively, while a solid dispersion comprising ospemifene, copovidone, and Cremophor® EL had increased solubility of 1995, 2077×, and 117× in water, 0.1 N HCl, and 50 mM PO$_4$, pH 6.8, respectively.

TABLE VII

Solubility Results of Solid Dispersions with Surfactants

| | Solubility (µg/mL) | | |
|---|---|---|---|
| | Water | 0.1N HCl | 50 mM PO$_4$, pH 6.8 |
| Ospemifene + Copovidone + Poloxamer (1:2:2) | | | |
| OSP/Copovidone/Poloxamer - Physical Mixture (PM) | 0.2 | 0.2 | 0.1 |
| OSP/Copovidone/Poloxamer - Solid Dispersion (SD) | 60.5 | 54.8 | 30.2 |
| Solubility Enhancement Ratio of SD/PM | 302x | 274x | 302x |
| Solubility Enhancement Ratio of SD/API alone | 1513x | 1827x | 1007x |
| Ospemifene + Copovidone + Sodium docusate (1:2:2) | | | |
| OSP/Copovidone/Sodium docusate - Physical Mixture (PM) | 3.9 | 6.1 | 4.9 |
| OSP/Copovidone/Sodium docusate - Solid Dispersion (SD) | NA | 9.7 | 2.2 |
| Solubility Enhancement Ratio of SD/PM | NA | NA | NA |
| Solubility Enhancement Ratio of SD/API alone | NA | 323x | 73x |
| Ospemifene + Copovidone + Span 20 (1:2:2) | | | |
| OSP/Copovidone/Span® 20 - Physical Mixture (PM) | 2.5 | 0.1 | 0.4 |
| OSP/Copovidone/Span® 20 - Solid Dispersion (SD) | 3.3 | 0.3 | 0.0 |
| Solubility Enhancement Ratio of SD/PM | NA | 3x | NA |
| Solubility Enhancement Ratio of SD/API alone | 83x | 10x | NA |
| Ospemifene + Copovidone + Span® 20 (1:3.4:0.6) | | | |
| OSP/Copovidone/Span® 20 - Physical Mixture (PM) | 1.0 | 0.1 | NA |
| OSP/Copovidone/Span® 20 - Solid Dispersion (SD) | 2.1 | NA | 1.6 |
| Solubility Enhancement Ratio of SD/PM | 2x | NA | NA |
| Solubility Enhancement Ratio of SD/API alone | 53x | NA | 53x |
| Ospemifene + Copovidone + Span 80 (1:3.4:0.6) | | | |
| OSP/Copovidone/Span® 80 - Physical Mixture (PM) | 1.4 | 3.7 | 0.2 |
| OSP/Copovidone/Span® 80 - Solid Dispersion (SD) | 6.3 | 4.9 | 0.7 |
| Solubility Enhancement Ratio of SD/PM | 5x | NA | 4 |
| Solubility Enhancement Ratio of SD/API alone | 158x | 163x | 23x |
| Ospemifene + Copovidone + Tween® 80 0:3.4:0.6) | | | |
| OSP/Copovidone/Tween® 80 - Physical Mixture (PM) | 2.8 | 2.8 | 2.6 |
| OSP/Copovidone/Tween® 80 - Solid Dispersion (SD) | 30.9 | 18.3 | 13.8 |
| Solubility Enhancement Ratio of SD/PM | 11x | 7x | 5x |
| Solubility Enhancement Ratio of SD/API alone | 773x | 610x | 460x |
| Ospemifene + Copovidone + Cremophor® EL (1:3.4:0.6) | | | |
| OSP/Copovidone/Cremophor® EL - Physical Mixture (PM) | 2.7 | 1.4 | 1.6 |
| OSP/Copovidone/Cremophor® EL - Solid Dispersion (SD) | 79.8 | 62.3 | 3.5 |
| Solubility Enhancement Ratio of SD/PM | 30x | 45x | 2x |
| Solubility Enhancement Ratio of SD/API alone | 1995x | 2077x | 117x |
| Ospemifene + Povidone + Sodium docusate (1:2:2) | | | |
| OSP/Povidone/Sodium docusate - Physical Mixture (PM) | 0.1 | 8.1 | 2.4 |
| OSP/Povidone/Sodium docusate - Solid Dispersion (SD) | 9.5 | 0.7 | 2.5 |
| Solubility Enhancement Ratio of SD/PM | 95x | NA | NA |
| Solubility Enhancement Ratio of SD/API alone | 238X | 23x | 83X |
| Ospemifene + Povidone + Span® 20 (1:2:2) | | | |
| OSP/Povidone/Span20 - Physical Mixture (PM) | 2.7 | 0.3 | 0.7 |
| OSP/Povidone/Span20 - Solid Dispersion (SD) | NA | 1.3 | 6.8 |
| Solubility Enhancement Ratio of SD/PM | NA | 4x | 10x |
| Solubility Enhancement Ratio of SD/API alone | NA | 43x | 227x |
| Ospemifene + Povidone + Poloxamer 407 (1:2:2) | | | |
| OSP/Povidone/Poloxamer407 - Physical Mixture (PM) | 1.6 | NA | 3.3 |
| OSP/Povidone/Poloxamer407 - Solid Dispersion (SD) | 11.4 | 1.6 | 1.2 |
| Solubility Enhancement Ratio of SD/PM | 7x | NA | NA |
| Solubility Enhancement Ratio of SD/API alone | 285x | 53x | 40x |
| Ospemifene + Povidone + Span® 20 (1:3.4:0.6) | | | |
| OSP/Povidone/Span20 - Physical Mixture (PM) | 0.5 | NA | 0.2 |
| OSP/Povidone/Span20 - Solid Dispersion (SD) | 2.7 | 0.5 | 3.9 |
| Solubility Enhancement Ratio of SD/PM | 5X | NA | 20x |
| Solubility Enhancement Ratio of SD/API alone | 68X | 17X | 130X |
| Ospemifene + Povidone + Span® 80 (1:3.4:0.6) | | | |
| OSP/Povidone/Span80 - Physical Mixture (PM) | 0.6 | NA | 0.1 |
| OSP/Povidone/Span80 - Solid | 4.4 | NA | 7.8 |

TABLE VII-continued

Solubility Results of Solid Dispersions with Surfactants

| | Solubility (µg/mL) | | |
| --- | --- | --- | --- |
| | Water | 0.1N HCl | 50 mM PO$_4$, pH 6.8 |
| Dispersion (SD) | | | |
| Solubility Enhancement Ratio of SD/PM | 7x | NA | 78x |
| Solubility Enhancement Ratio of SD/API alone | 110x | NA | 260x |
| Ospemifene + Povidone + Tween ® 80 (1:3.4:0.6) | | | |
| OSP/Povidone/Tween80 - Physical Mixture (PM) | 3.3 | 1.6 | 2.6 |
| OSP/Povidone/Tween80 - Solid Dispersion (SD) | 1.2 | 0.2 | 3.0 |
| Solubility Enhancement Ratio of SD/PM | NA | NA | NA |
| Solubility Enhancement Ratio of SD/API alone | 30x | 7x | 100x |

Example 4: Pharmacokinetic Behavior in Simulated Fed and Fasted Conditions

To investigate the in-vivo absorption process of ospemifene in the GI tract, a dissolution method using simulated GI fluids (FaSSIF and FeSSIF) was developed to simulate drug dissolution in-vivo. The abbreviation "FaSSIF" stands for fasted state simulated intestinal fluid, while the abbreviation "FeSSIF" stands for fed state simulated intestinal fluid. The solubility of micronized ospemifene in aqueous pH 6.8 phosphate buffer medium is <0.01 mg/mL. FaSSIF and FeSSIF media are commercially available from Biorelevant and were used according to the manufacturer's instructions.

Micro dissolution was conducted in a centrifuge vial containing 1.5 mL of dissolution medium (either FaSSIF or FeSSIF) at room temperature. The target concentration was 0.024 mg/ml for sink condition and 0.24 mg/mL for supersaturating condition, the latter being equivalent to a 60 mg dose in 250 mL of liquid. See for example Kostwicz et al., 2002. The vials were centrifuged at 30 min, 1, 2 and 3 hour(s) at 14,000 rpm for one minute and 50 µL of supernatant was transferred to an HPLC vial and diluted with 50 µL acetonitrile and assayed by HPLC.

An Agilent 1100 series HPLC equipped with a Waters Symmetry Shield C18 150×4.6 mm 3.5 µm column equilibrated at 30° C. was used. The detector was set at 235 nm. Two mobile phases were used, mobile phase A and mobile phase B. Mobile phase A was 800/200/40 (v/v/v) deionized water/acetonitrile/tetrahydrofuran and mobile phase B was 100% acetonitrile.

For impurity analysis, the flow rate of the mobile phases was 0.85 mL/min, the injection volume was 10 µl and the gradient program was as follows:

| Time (mins) | % A | % B |
| --- | --- | --- |
| 0 | 53 | 47 |
| 17 | 30 | 70 |
| 18 | 30 | 70 |
| 32 | 53 | 47 |
| 35 | 53 | 47 |

For drug content analysis, the same HPLC column and mobile phases were used but the flow rate of the mobile phases was 1 ml/min, the injection volume was 7 µL and the gradient program was as follows:

| Time (mins) | % A | % B |
| --- | --- | --- |
| 0 | 30 | 70 |
| 4 | 30 | 70 |
| 4.01 | 10 | 90 |
| 5 | 10 | 90 |
| 5.01 | 30 | 70 |
| 8 | 30 | 70 |

For ospemifene alone, the solubility was about 2-3 fold higher in FeSSIF than in FaSSIF, and the amount of drug in solution remains relatively stable for at least 2-3 hours. FIG. 1. For micronized ospemifene, the solubility in FeSSIF (0.045 mg/mL) is about 4 fold higher than in FaSSIF (0.01 mg/mL at 2 hr). These results are consistent with the literature (Koskimies et al.), as well as the package insert for Osphena® tablets (ospemifene tablets for oral use), which states that food increases the bioavailability of ospemifene by approximately 2-3 fold.

A. Solvent Casting

A screening study to assess suitable hydrophilic carriers for making ospemifene solid dispersions was conducted. Initially, ospemifene solid dispersion were made with the following hydrophilic carriers: HPMC 603, PVP K30, PVPVA (PVPVA64), HPC SSL, Eudragit® L100-55, HPMCAS LF, Poloxamer 407, HP-55, and Soluplus® using spray-drying and hot-melt extrusion methods of preparation.

Films were casted using drug-polymer ethanol solution (1:4 w/w for drug:hydrophilic carrier) and dried in ambient room conditions. The dried films were placed in a chamber either at 40° C. and ambient humidity, or 40° C. and 75% relative humidity (RH) for up to 90 hours in order to stabilize the film. After storage, films were examined for visual clarity and crystallinity using polarized microscopy.

B. Spray Drying

Based on an assessment of the cast films produced, solid dispersions of ospemifene and the following hydrophilic carriers Soluplus®, PVPVA, HPC SL, Eudragit® L100-55, HPMCAS LF, PVP K30, and HP-55 were prepared by the solvent evaporation method. For the spray-drying technique, ospemifene and hydrophilic carriers at 2:8 w/w ratio were dissolved in ethanol or ethanol/water (8:2) (for cellulose carriers) at about 5% solid content and were spray dried using the Büchi B-290 system under the following conditions: Inlet temperature set to 50-80° C., aspirator at 70-100%, pump speed at 10-30% and nozzle cleaning set to 4. The spray dried solids were dried at 40° C. in a forced air oven after being transferred onto a wide petri dish covered with aluminum foil. All of the samples were kept in an amber bottle at room temperature until further use. The batch size was about 5-10 g.

C. Hot-Melt Extrusion

The hot melt extrusion method was conducted using physical blends of drug/hydrophilic carrier (2:8 (w/w)) using Thermo Haake Minilab microcompounder under the following conditions: Temperature setting: 120-180° C., Motor speed setting at 100-200 L/min. Hot melt extruded solids were ground using a grinder after solidification. All of the samples were kept in an amber bottle at room temperature until further use. The batch size was around 10 g.

The samples made by solvent casting, spray drying and hot melt extrusion were then stored at 40° C. and 75% RH (open and closed conditions) for 78 hours and analyzed by HPLC. The HPLC results showed the ospemifene is generally chemically compatible with all of the excipients tested, with the exception of HP-55, where impurities nearing 5% of the total sample were observed. For all other combinations tested, impurities were less than or equal to 0.4%.

D. Ospemifene/Copovidone Solid Dispersion

Figure 2:
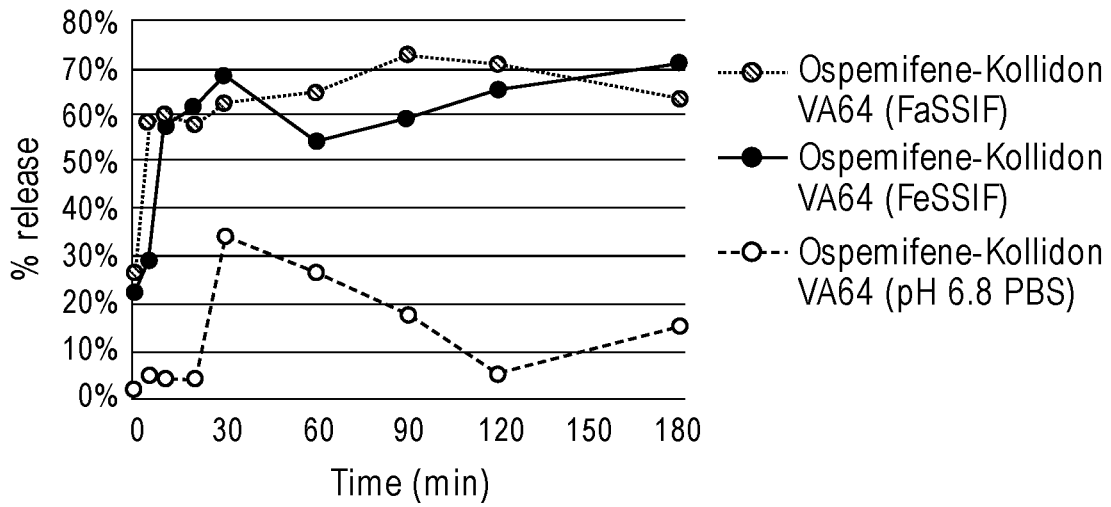
FIG. 2 depicts the dissolution kinetics of ospemifene from a solid dispersion comprising copovidone (Kollidon® V64) in FeSSIF, FaSSIF, and PBS, pH 6.8.

A solid dispersion of ospemifene and copovidone (PVPVA64) was manufactured using the solvent evaporation method as described in Example 1 and its dissolution was analyzed in FaSSIF and FeSSIF. The drug was released at a similar rate and extent in either FaSSIF or FeSSIF, with about 60-70% of the dose released within 10 minutes (at 0.024 mg/mL theoretical concentration), and release was more rapid than was observed when ospemifene was suspended in a pH 6.8 phosphate buffer. FIG. 2. By contrast, food is known to increase the bioavailability of ospemifene in other formulations (e.g., Osphena®) by 2-3 fold.

E. Ospemifene/Soluplus® Solid Dispersion

Figure 3:
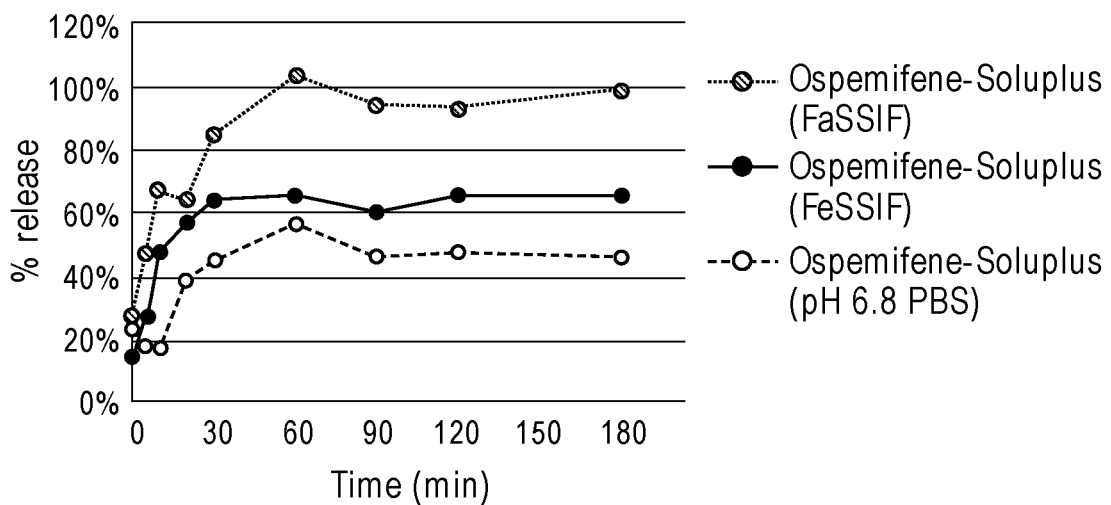
FIG. 3 depicts the dissolution kinetics of ospemifene from a solid dispersion comprising Soluplus® in FeSSIF, FaSSIF, and PBS, pH 6.8.

A solid dispersion of ospemifene and Soluplus® was manufactured using the solvent evaporation method as described in Example 1 and its dissolution was analyzed in FaSSIF and FeSSIF. For this solid dispersion, nearly 100% of the dose was released into FeSSIF, compared to 60% release into FaSSIF, and about 45% release into a pH 6.8 phosphate buffer. FIG. 3.

F. Ospemifene/HPMCAS Solid Dispersion

Figure 4:
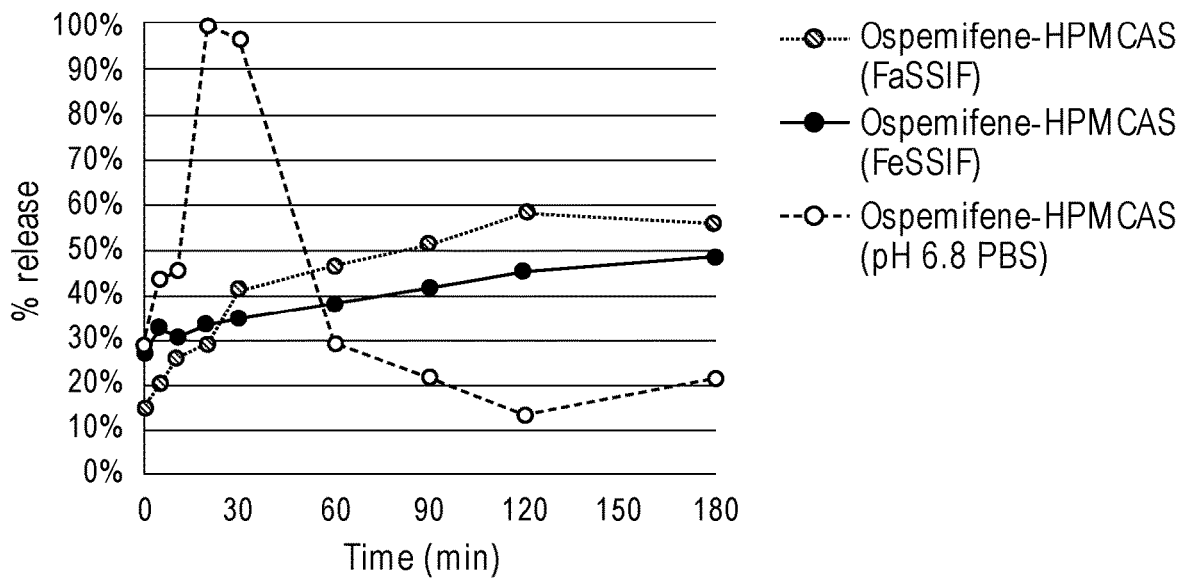
FIG. 4 depicts the release kinetics of ospemifene from a solid dispersion comprising HPMCAS in FeSSIF, FaSSIF, and PBS, pH 6.8.

A solid dispersion of ospemifene and HPMCAS was manufactured using the solvent evaporation method as described in Example 1 and its dissolution was analyzed in FaSSIF and FeSSIF. In a solid dispersion of ospemifene and HPMCAS, release kinetics were significantly slower, with it taking nearly two hours to reach maximal release in either FaSSIF or FeSSIF. FIG. 4. In addition, only about 50-60% of the theoretical dose was released, although surprisingly, greater release was observed in FaSSIF than in FeSSIF. FIG. 4. This is in contrast to other studies with ospemifene, where solubility is generally significantly better in FeSSIF.

G. Ospemifene/Povidone Solid Dispersion

Figure 5:
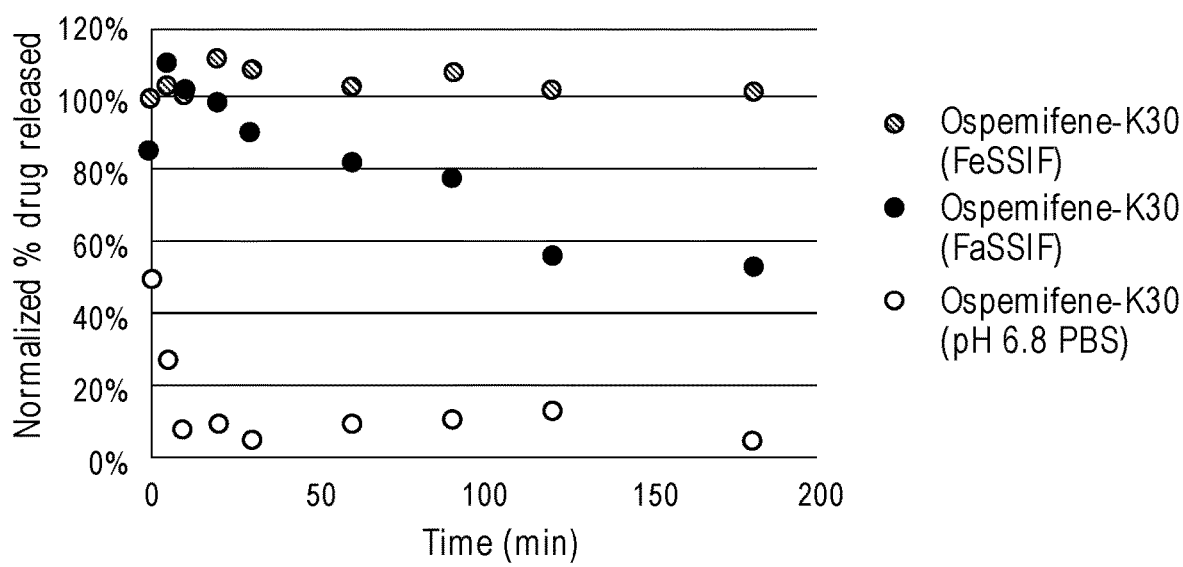
FIG. 5 depicts the release kinetics of ospemifene from a solid dispersion comprising povidone (PVP K30) in FeSSIF, FaSSIF, and PBS, pH 6.8.

A solid dispersion of ospemifene and povidone (PVP K30) was manufactured using the solvent evaporation method as described in Example 1 and its dissolution was analyzed in FaSSIF and FeSSIF. For this solid dispersion, a high rate of drug release was initially observed for both FaSSIF and FeSSIF. However, a slight reduction in the drug concentration over time was observed under FaSSIF conditions, probably due to precipitation of drug from the dissolution medium. Similarly, the drug was rapidly released in pH 6.8 buffer over approximately the first 30 minutes. However, the release rate slowed after 30 minutes as compared to the solid dispersion in FeSSIF and FaSSIF, due, perhaps, to rapid drug precipitation over time. FIG. 5.

H. Ospemifene/Hydroxypropylcellulose Solid Dispersion

Figure 6:
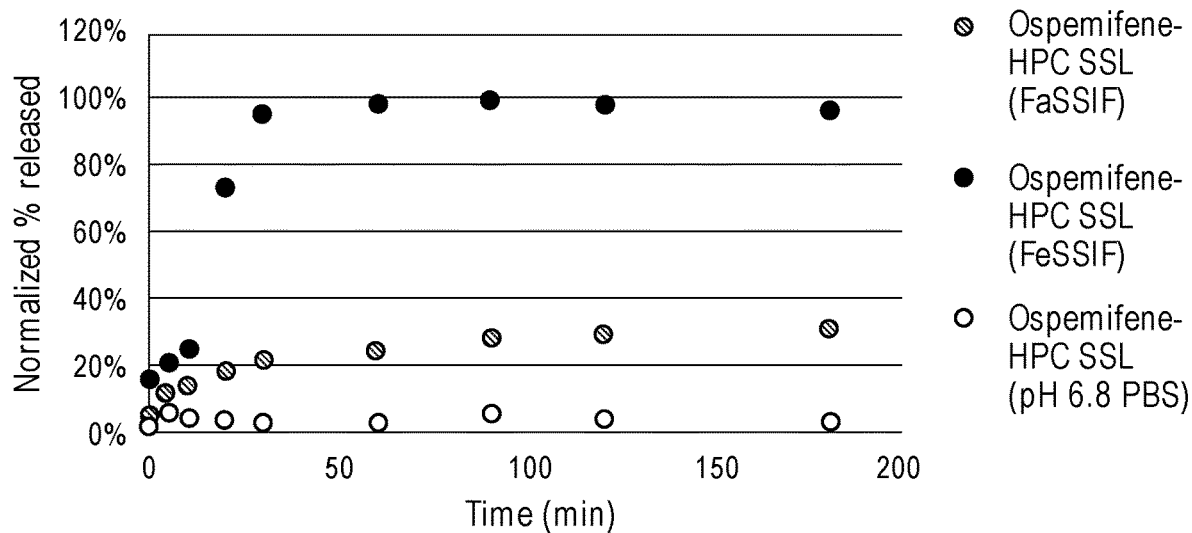
FIG. 6 depicts the release kinetics of ospemifene from a solid dispersion comprising HPC in FeSSIF, FaSSIF, and PBS, pH 6.8.

A solid dispersion of ospemifene and hydroxypropylcellulose (HPC-SSL) was manufactured using the solvent evaporation method as described in Example 1 and its dissolution was analyzed in FaSSIF and FeSSIF. For the solid dispersion made with hydroxypropylcellulose, the ospemifene dissolution rate and extent of release were widely different between the FaSSIF, FeSSIF, and pH 6.8 buffer conditions. The ranking order of drug release extent is FeSSIF>FaSSIF>pH 6.8 buffer. The dissolution rate was fastest in FeSSIF, reaching a plateau within 30 minutes and slowest in pH 6.8 buffer. FIG. 6.

I. Ospemifene/Hydroxypropyl Methylcellulose Phthalate Solid Dispersion

Figure 7:
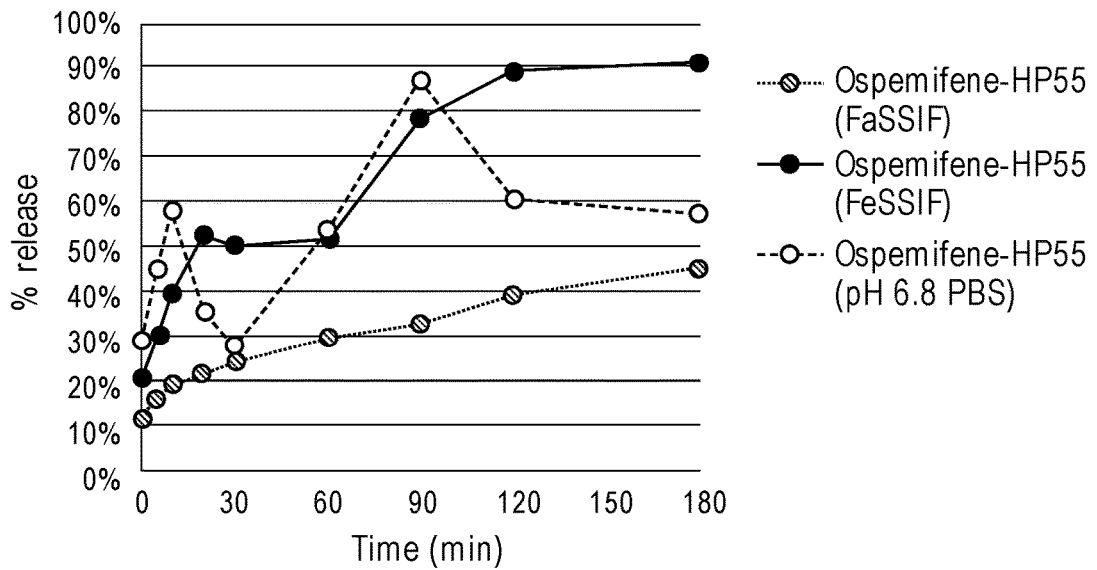
FIG. 7 depicts the release kinetics of ospemifene from a solid dispersion comprising HP-55 in FeSSIF, FaSSIF, and PBS, pH 6.8.

A solid dispersion of ospemifene and hydroxypropyl methylcellulose phthalate (HP-55) was manufactured using the solvent evaporation method as described in Example 1 and its dissolution was analyzed in FaSSIF and FeSSIF. Similar to ospemifene solid dispersion made with HPM-CAS, the drug dissolution from solid dispersion made with HP-55 was relatively slow under both FeSSIF and FaSSIF conditions, reaching about 90% of target concentration in 120 minutes in FeSSIF. The release of drug in FaSSIF was slower than in FeSSIF. The dissolution of drug in pH 6.8 buffer was moderate, falling in between that of FeSSIF and FaSSIF, which behaved differently from that of HPMCAS and Eudragit® L100-55 in pH 6.8 buffer. FIG. 7.

J. Ospemifene/Eudragit® Solid Dispersion

Figure 8:
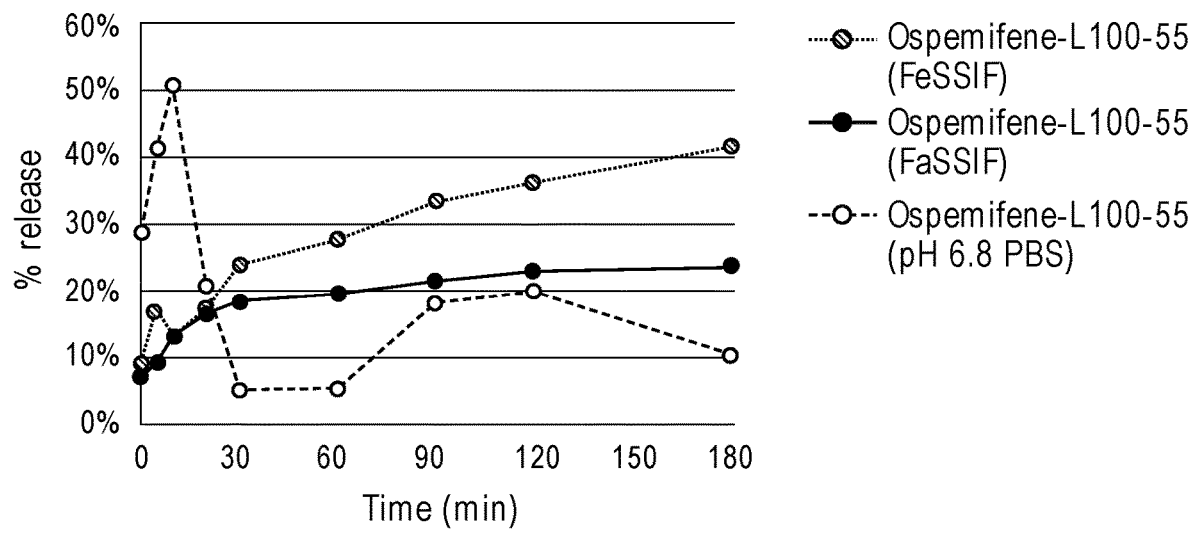
FIG. 8 depicts the release kinetics of ospemifene from a solid dispersion comprising Eudragit® L100-55 in FeSSIF, FaSSIF, and PBS, pH 6.8.

A solid dispersion of ospemifene and Eudragit® L100-55 was manufactured using the solvent evaporation method as described in Example 1 and its dissolution was analyzed in FaSSIF and FeSSIF. Similar to solid dispersion made with HPMCAS, the drug dissolution from solid dispersion made with Eudragit® L100-55 polymer was slow both under FeSSIF and FaSSIF, reaching about 40% of target concentration in 180 minutes in FeSSIF. The release of drug in FaSSIF was slower than in FeSSIF. The dissolution of drug in pH 6.8 buffer w as similar to that of HPMCAS, where a fast dissolution was observed initially, but the drug failed to maintain its supersaturated state. As a result, after reaching 50% of drug release within 10 minutes, the drug concentration rapidly fell to below 20%. FIG. 8.

Example 5: Effects of Surfactants on Dissolution Properties of Ospemifene Solid Dispersions After the initial hydrophilic carrier screening, various surfactants, including Span® 20, Span® 80, Tween® 80, Kolliphor® EL, and poloxamer 407, were added to ospemifene solid dispersions to evaluate their effects on release of ospemifene in either FaSSIF or FeSSIF. Specifically, the effects of different types and amounts of surfactant on the dissolution properties of ospemifene solid dispersions comprising copovidone (PVPVA), and povidone (PVP) were evaluated.

In addition, the combination of ospemifene and surfactant with copovidone (PVPVA64), povidone (PVP K30), and hydroxypropylcellulose (HPC-SSL) were also evaluated for solid dispersion formation.

The solid dispersions comprising the ternary mixture of ospemifene, surfactant, and hydrophilic carrier were made using the solvent evaporation method described in Example 1. Films were casted using a solid dispersion/ethanol solution (1:3.4:0.6 w/w/w for drug:hydrophilic carrier:surfactant). Using polarized microscopy, no crystallization was observed after storage at 40° C. for 72 hours. After storage at 40° C./75% RH open conditions, PVPVA appeared to have the best physical stability as compared to PVP and HPC film, as summarized in Table VIII. The ranking order was PVPVA>HPC>PVP.

TABLE VIII

Observations of films prepared on glass slides in stressed condition for 72 hours

| Polymer and/or surfactant | Storage condition for 72 hours | |
|---|---|---|
| | 40° C. | 40° C./75% RH |
| PVP K30 | All samples are clear and free of crystallinity by microscopic inspection | Visually, cloudy spots on the slide were observed. Needle like crystals were forming clusters |
| PVP K30-Span 20 | | Visually, cloudy spots were detected. Thin network of crystals were present |
| PVP K30-Span 80 | | Even though the film appears clear to the naked eye, long crystals in the shape of needles were present |
| PVP K30-Tween 80 | | Without the microscope, net-like growth was observed. Under the microscope, the net is actually long crystalline needles |
| PVPVA 64 | | Film appeared clear and no sign of crystallinity |
| PVPVA 64-Span 20 | | Film appeared clear and no sign of crystallinity |
| PVPVA 64-Span 80 | | Film appeared clear and no sign of crystallinity |
| PVPVA 64-Tween 80 | | Film appeared clear and no sign of crystallinity |
| HPC | | Film appeared clear and no sign of crystallinity |
| HPC-Span 20 | | Film appeared clear and no sign of crystallinity |
| HPC-Span 80 | | Film appeared cloudy. Long network of crystals were present |
| HPC-Tween 80 | | Film showed network like cracks. Long crystal needles were present |

Figure 9:
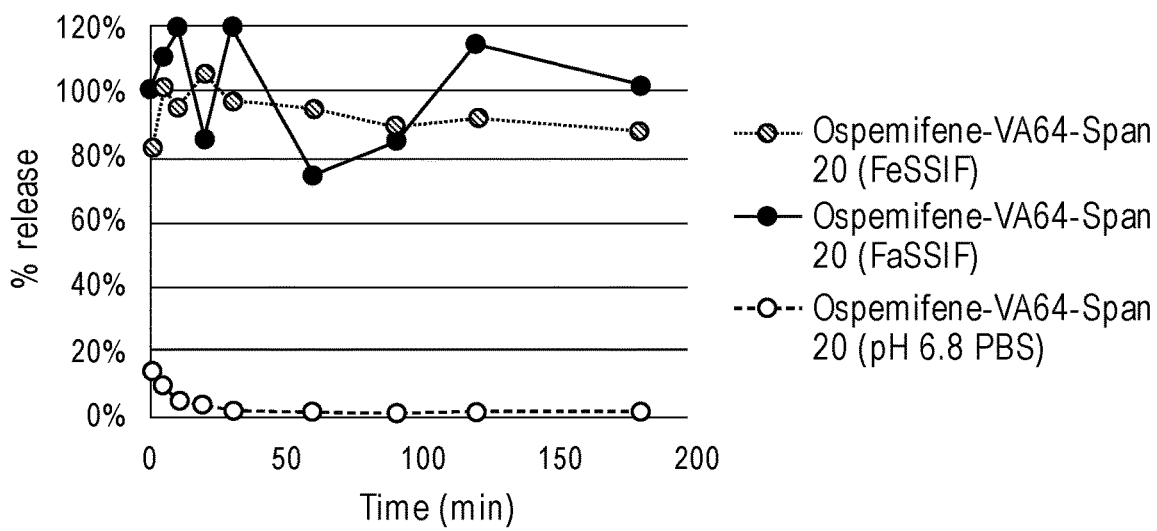
FIG. 9 depicts the release kinetics of ospemifene (target concentration of 0.024 mg/mL) from a solid dispersion comprising copovidone (PVPVA64) and Span 20 in FeSSIF, FaSSIF, and PBS, pH 6.5.
Figure 10:
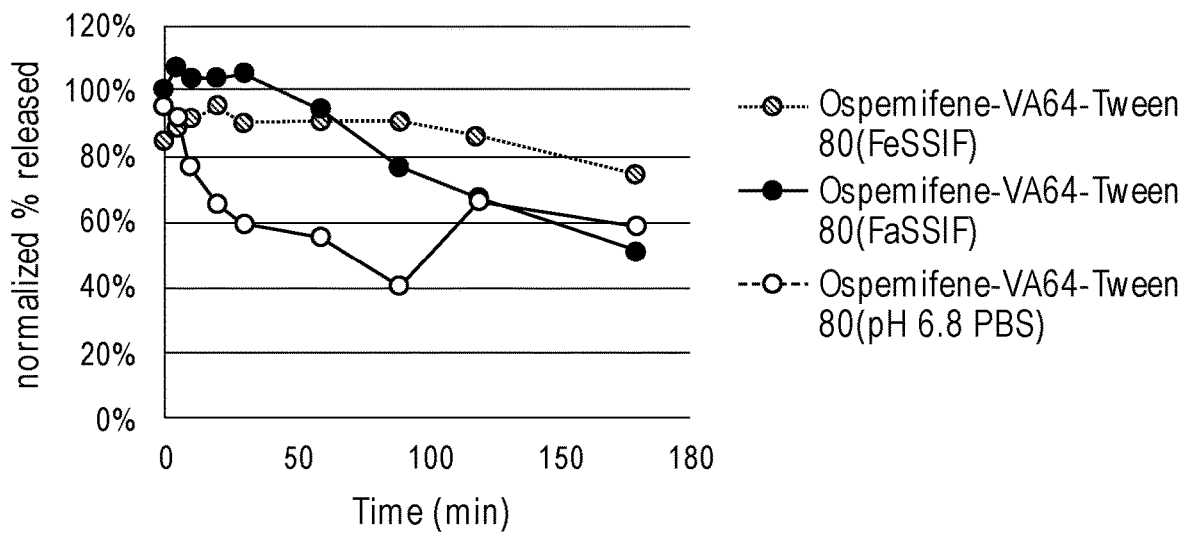
FIG. 10 depicts the release kinetics of ospemifene (target concentration of 0.024 mg/mL) from a solid dispersion comprising copovidone (PVPVA 64) and Tween 80 in FeSSIF, FaSSIF, and PBS, pH 6.8.
Figure 11:
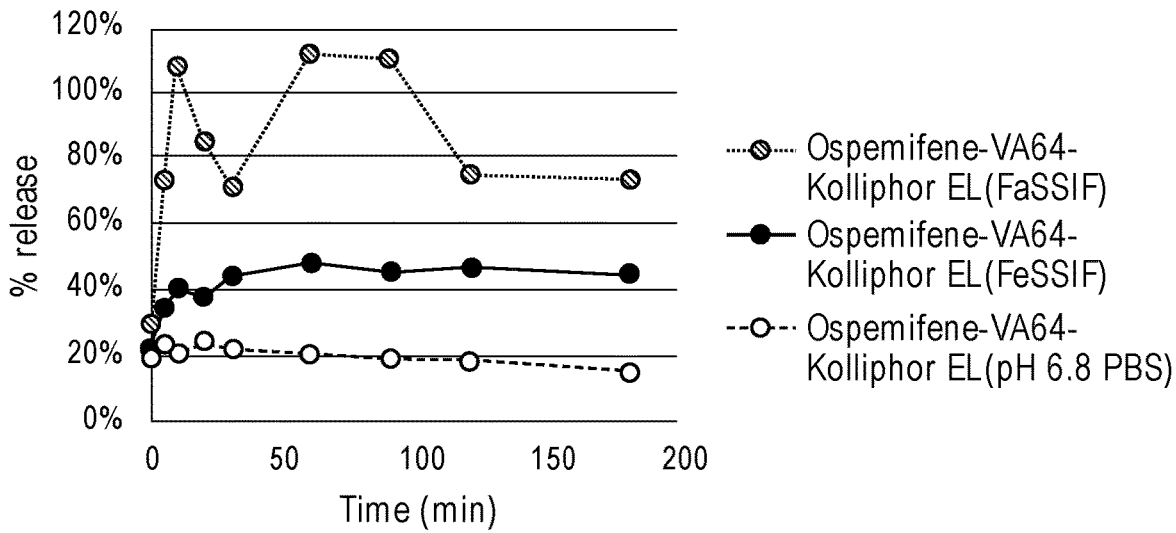
FIG. 11 depicts the dissolution kinetics of ospemifene (target concentration of 0.024 mg/mL) from a solid dispersion comprising copovidone (PVPVA 64) and Kolliphor EL FeSSIF, FaSSIF, and PBS, pH 6.8.

At a target concentration of 0.024 mg/mL, the addition of surfactant to a solid dispersion comprising ospemifene and copovidone (PVPVA64) (drug:carrier:surfactant 1:3.4:0.6), significantly improved the extent of drug release as compared to crystalline drug in all three media tested (FeSSIF, FaSSIF, and phosphate buffer, pH 6.8), particularly with the surfactants Tween® 80 and Kolliphor® EL. FIGS. 9-11. Unexpectedly, a solid dispersion comprising ospemifene, copovidone (PVPVA64), and Span® 20 (and to a lesser extent Tween® 80) showed nearly identical release kinetics in both FeSSIF and FaSSIF. FIGS. 9-10. This is consistent to the effect observed for ospemifene/copovidone solid dispersions without a surfactant. See FIG. 2. Similar effects were seen in solid dispersions comprising ospemifene, copovidone, and Tween® 80, although over time, there was evidence of loss of ospemifene from the dissolution medium, perhaps due to precipitation.

A solid dispersion comprising ospemifene, PVPVA64 and Kolliphor® EL (a non-ionic emulsifier) also surprisingly displayed greater release of drug into FaSSIF as compared to FeSSIF (80% versus 50%).

Figure 12:
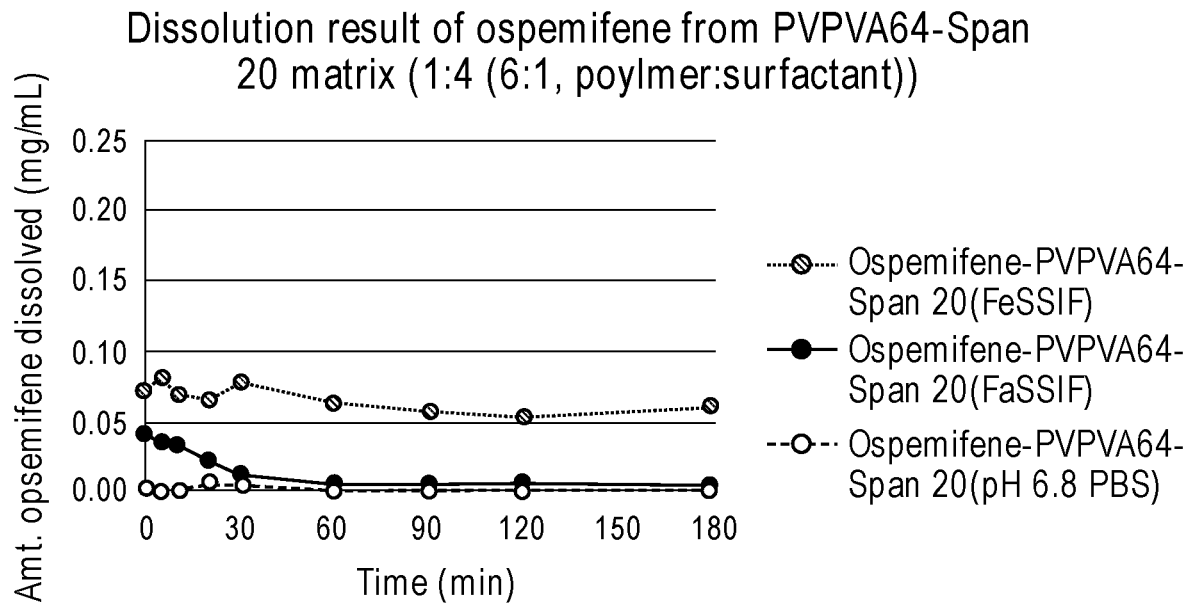
FIG. 12 depicts the dissolution kinetics of ospemifene (target concentration of 0.24 mg mL) from a solid dispersion comprising copovidone (PVPVA 64) and Span 20 in FeSSIF, FaSSIF, and PBS, pH 6.8.
Figure 13:
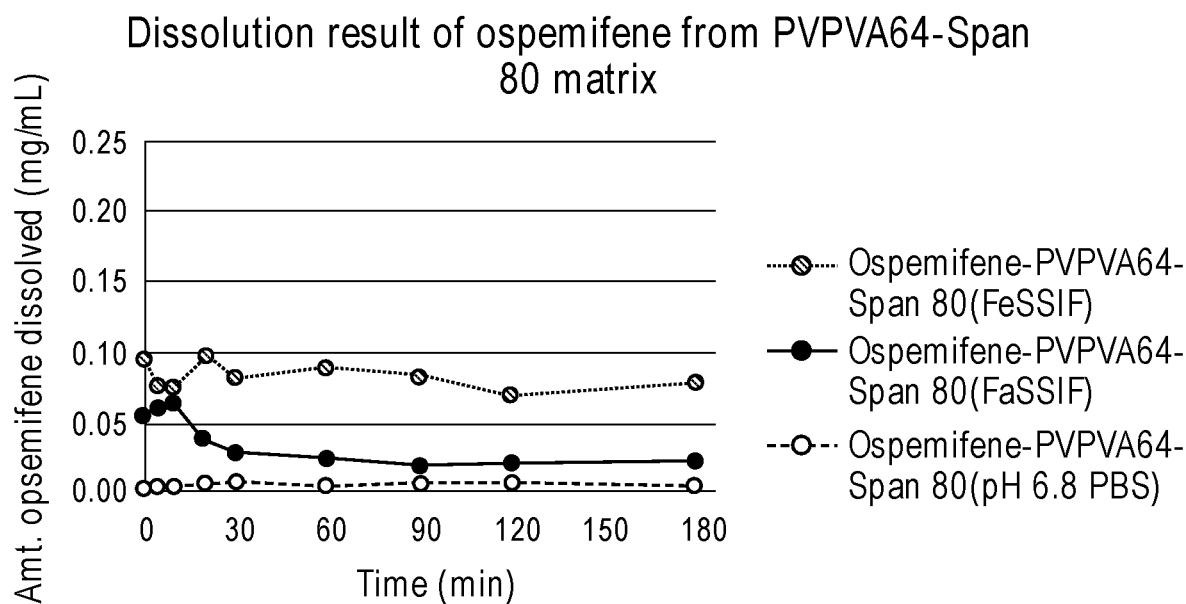
FIG. 13 depicts the dissolution kinetics of ospemifene (target concentration of 0.24 mg mL) from a solid dispersion comprising copovidone (PVPVA 64) and Span 80 in FeSSIF, FaSSIF, and PBS, pH 6.8.
Figure 14:
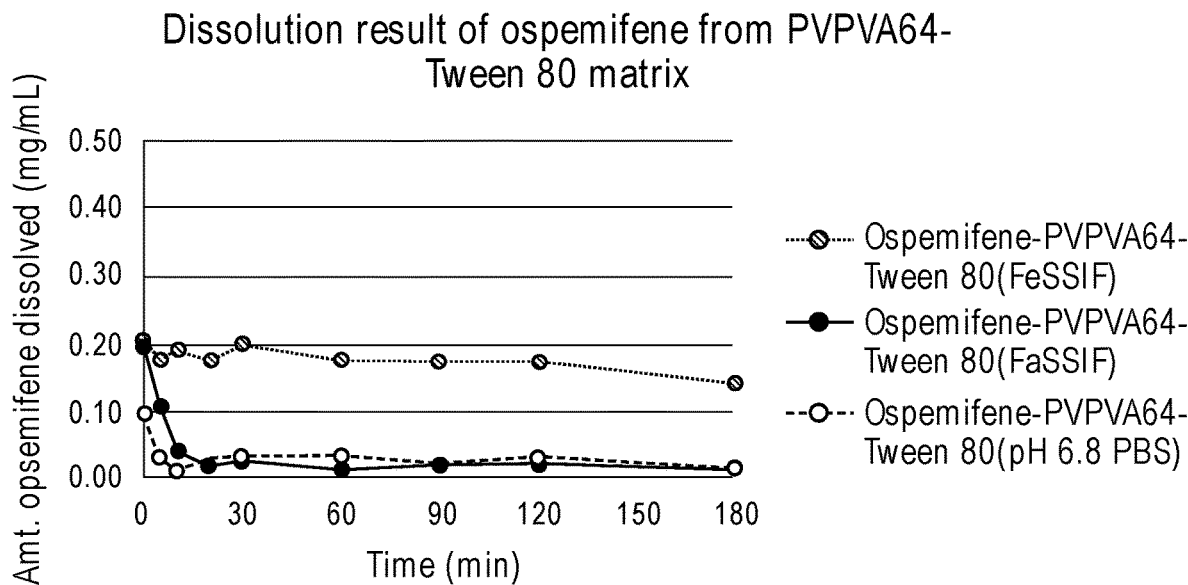
FIG. 14 depicts the dissolution kinetics of ospemifene (target concentration of 0.24 mg mL) from a solid dispersion comprising copovidone (PVPVA 64) and Tween 80 FeSSIF, FaSSIF, and PBS, pH 6.8.

Additional studies were conducted at a super-saturated target concentration, equivalent to 60 mg of osmepifene in 250 mL of medium (0.24 mg/mL). Compared to the dissolution of micronized ospemifene under the same super-saturation concentration (0.24 mg/mL), solid dispersions containing ospemifene, copovidone (PVPVA64), and a surfactant (Span® 20, Span® 80, and Tween® 80) (copovidone:surfactant=6:1) (drug:carrier:surfactant=1:3.4:0.6) showed significant improvement in the extent of drug dissolution particularly in FeSSIF media. However, the extent of drug release in pH 6.8 phosphate buffer did not show an improvement. FIGS. 12-14.

Figure 15:
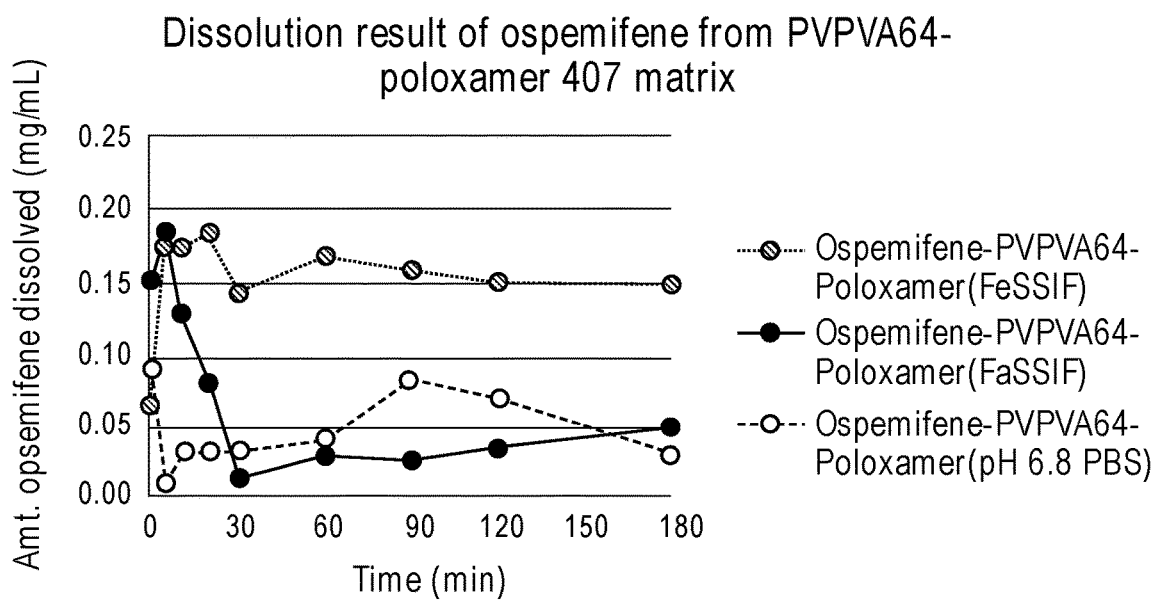
FIG. 15 depicts the dissolution kinetics of ospemifene from a solid dispersion comprising copovidone (PVPVA 64) 64 and poloxamer 407 in FeSSIF, FaSSIF, and PBS, pH 6.8.
Figure 16:
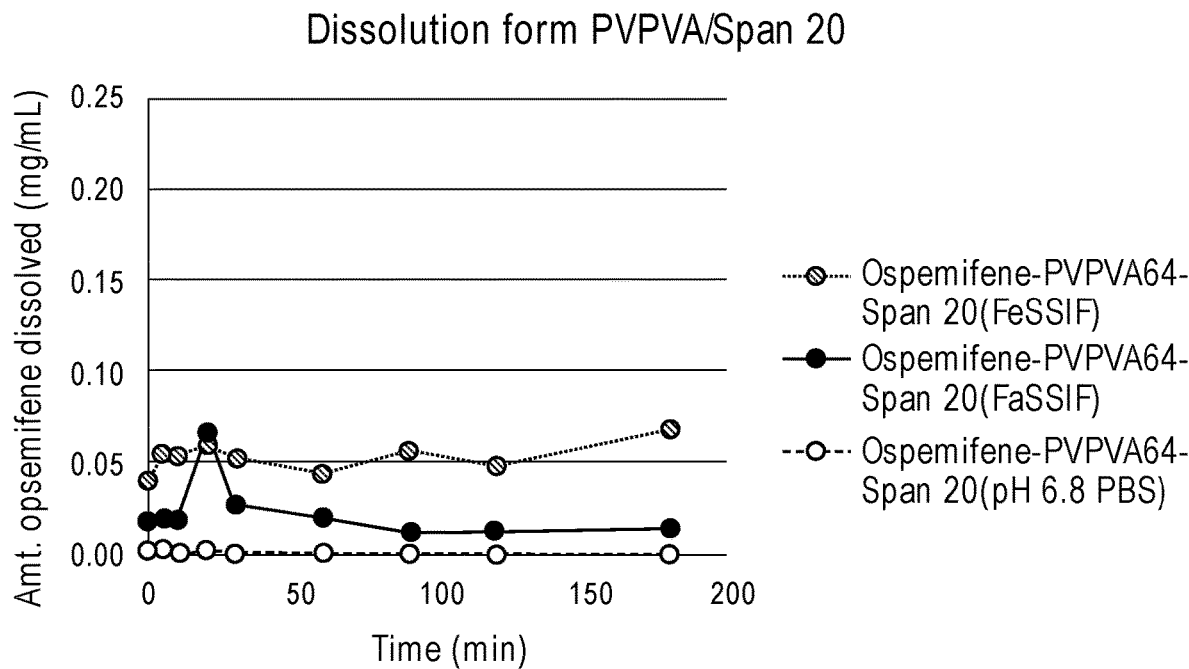
FIG. 16 depicts the dissolution kinetics of ospemifene from a solid dispersion comprising copovidone (PVPVA 64) and Span 20 (drug:carrier:surfactant 1:2:2) in FeSSIF, FaSSIF, and PBS, pH 6.8.
Figure 17:
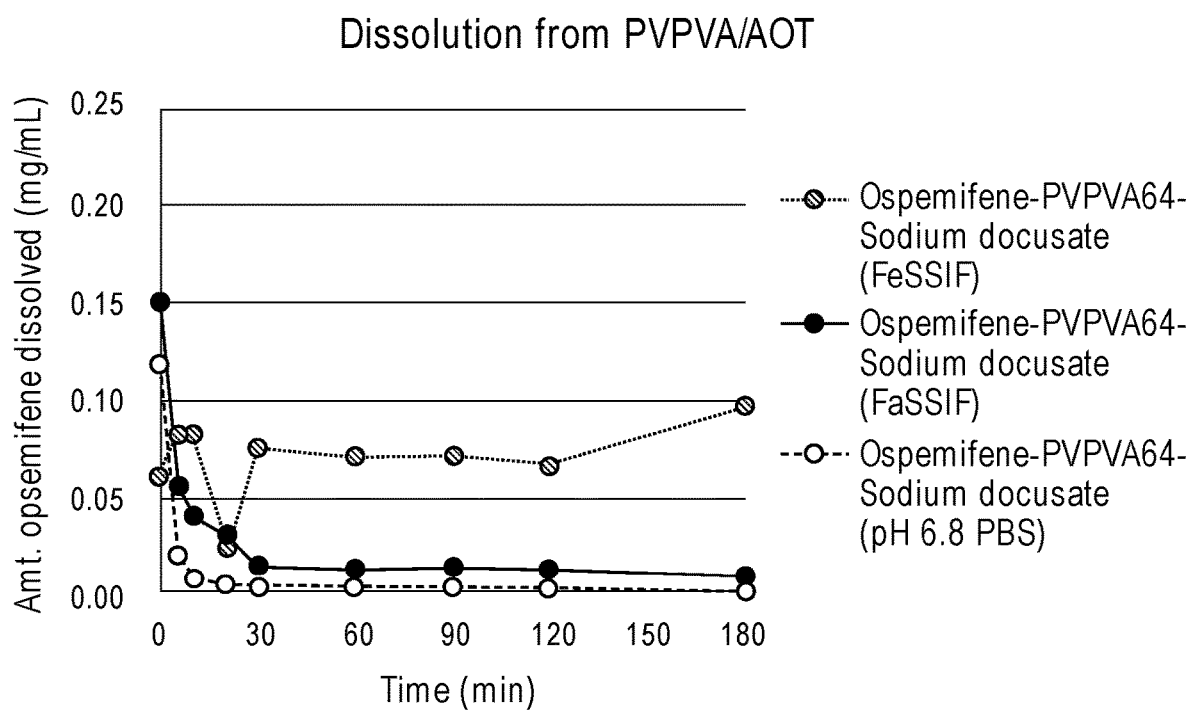
FIG. 17 depicts the dissolution kinetics of ospemifene from a solid dispersion comprising copovidone (PVPVA 64) and sodium docusate (AOT) in FeSSIF, FaSSIF, and PBS, pH 6.8.

In vitro dissolution studies were conducted with ospemifene solid dispersions made with other surfactants (drug:carrier:surfactant=1:2:2) including Poloxamer 407 and sodium docusate. Significant improvement in the dissolution in all three media was observed with a solid dispersion made using copovidone (PVPVA64)/Poloxamer 407 as the matrix. FIG. 15. For solid dispersions comprising ospemifene, copovidone, and sodium docusate, significant improvement in dissolution was observed in FeSSIF medium but not in phosphate buffer, pH 6.8 and FaSSIF medium. FIG. 17. For a solid dispersion comprising ospemifene, copovidone, and Span 20, where the level of surfactant was increased (drug:polymer:surfactant=1:2:2), significant improvement in dissolution was observed in FeSSIF medium but not in phosphate buffer, pH 6.8 and FaSSIF medium as compared to a solid dispersion comprising ospemifene, copovidone, and Span® 20 at a lower concentration (drug:polymer:surfactant=3.4:0.6). FIG. 16.

Figure 18:
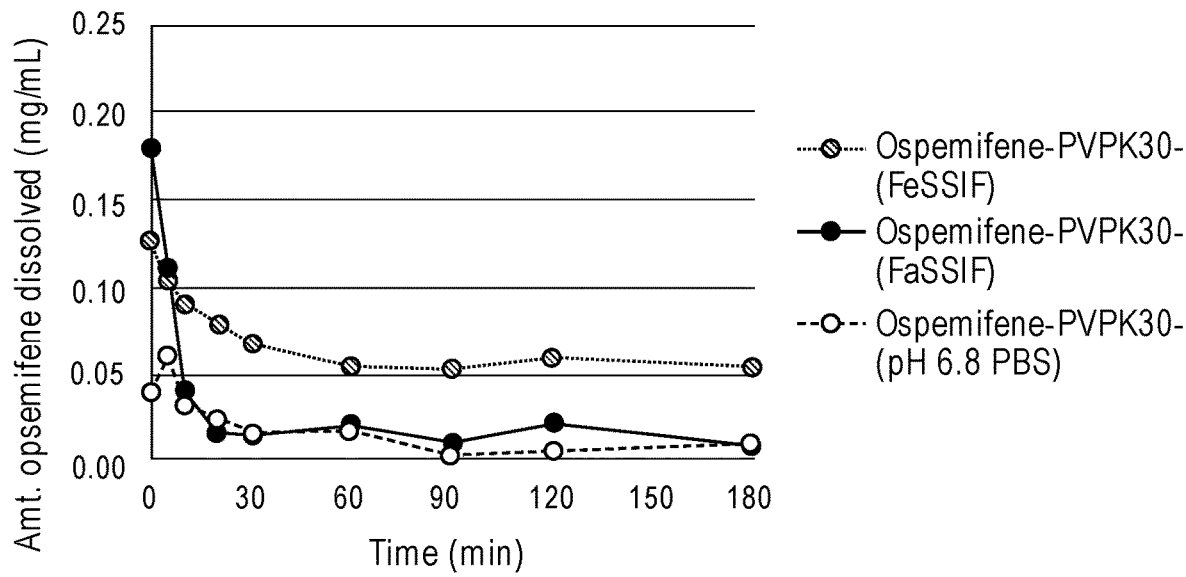
FIG. 18 depicts the dissolution kinetics of ospemifene (target concentration of 0.24 mg/mL) from a solid dispersion comprising povidone (PVP K30) in FeSSIF, FaSSIF, and PBS. pH 6.8.
Figure 19:
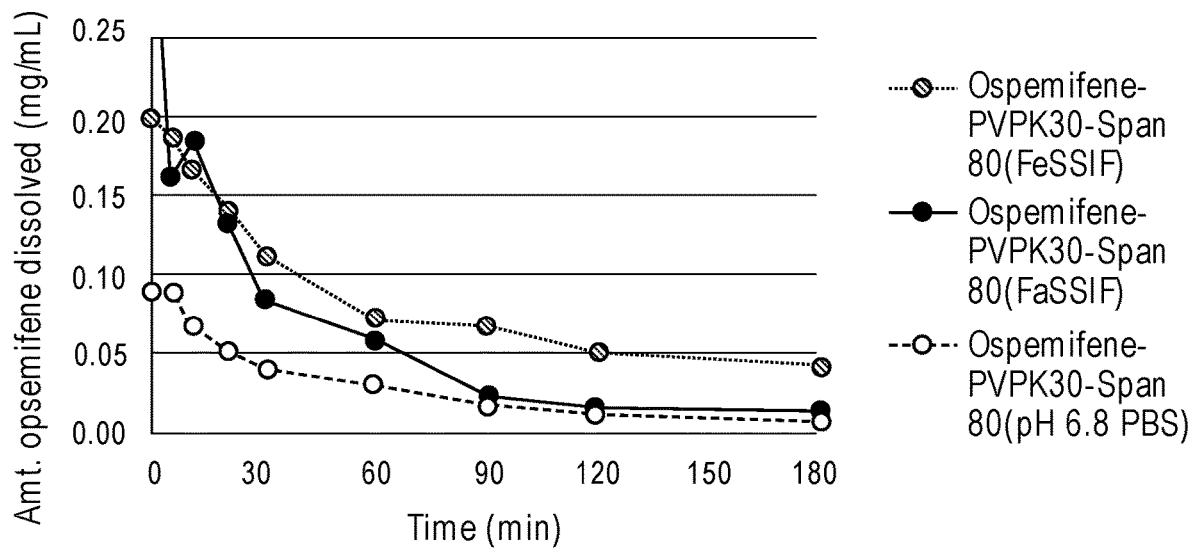
FIG. 19 depicts the dissolution kinetics of ospemifene from a solid dispersion comprising povidone (PVP K30) and Span 80 (drug:carrier:surfactant 1:3.4:0.6) in FeSSIF, FaSSIF, and PBS, pH 6.8.
Figure 20:
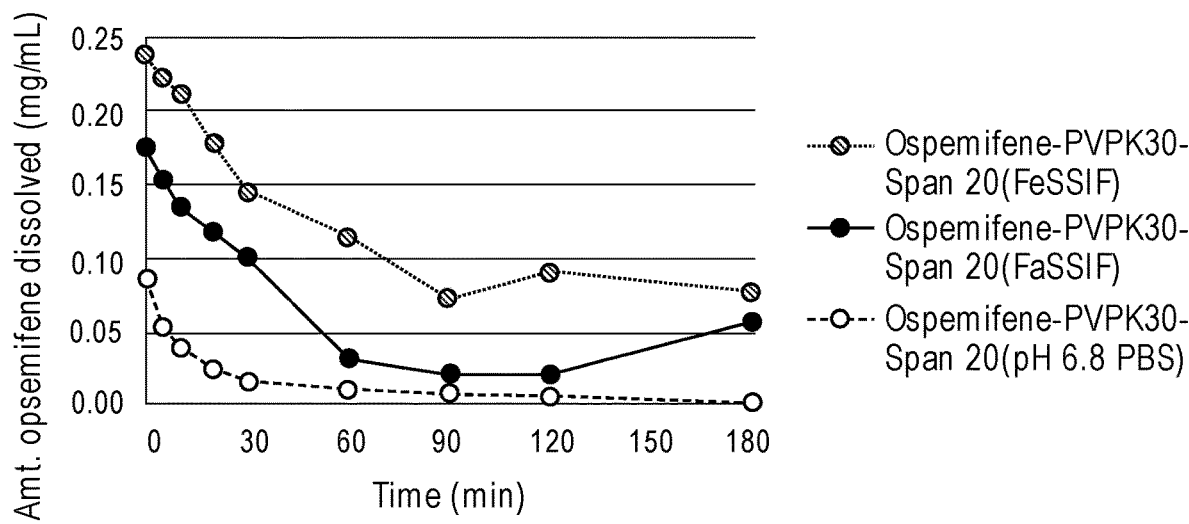
FIG. 20 depicts the dissolution kinetics of ospemifene from a solid dispersion comprising povidone (PVP K30) and Span 20 (drug:carrier:surfactant 1:3.4:0.6) in FeSSIF, FaSSIF, and PBS, pH 6.8.
Figure 21:
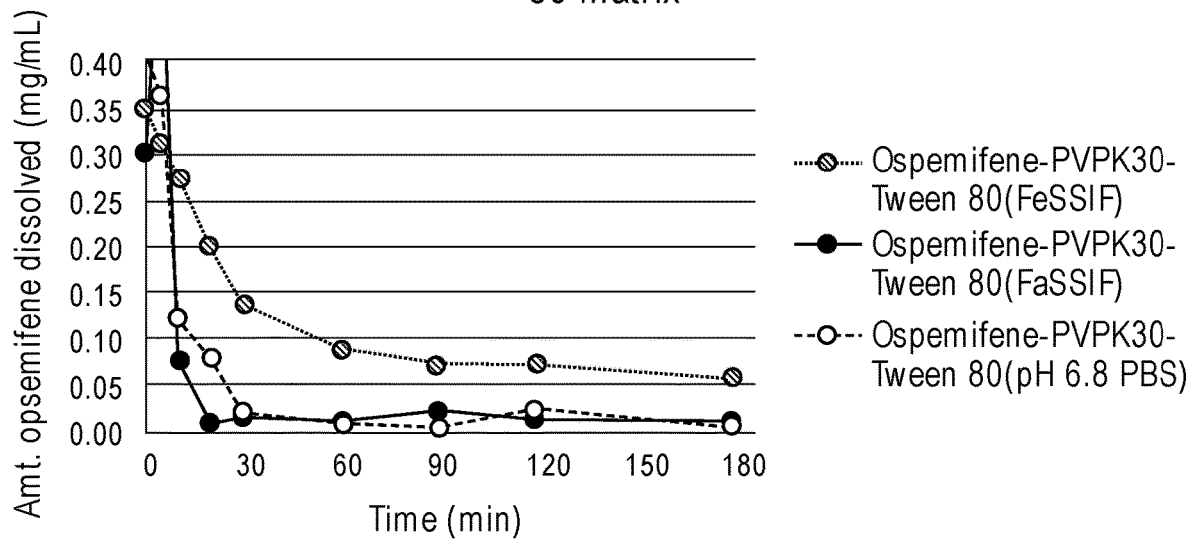
FIG. 21 depicts the dissolution kinetics of ospemifene from a solid dispersion comprising povidone (PVP K30) and Tween 80 (drug:carrier:surfactant 1:3.4:0.6) in FeSSIF, FaSSIF, and PBS, pH 6.8.

Similar studies were conducted with solid dispersions comprising ospemifene, povidone (PVP K30), and a surfactant. At a target concentration of 0.24 mg/mL, solid dispersion made with ospemifene and povidone showed a fast initial dissolution rate in all three dissolution media. FIG. 18. However, a rapid reduction in concentration over time was observed. FIG. 18. Adding surfactant (Span® 20, Span® 80, Tween® 80) to the solid dispersion (drug:polymer:surfactant=1:3.4:0.6), significantly prolonged drug supersaturation (drug dissolved in medium is higher than the thermodynamic solubility of the crystalline drug), particularly with surfactant Span® 80 and Span® 20. FIGS. 19-21.

Figure 22:
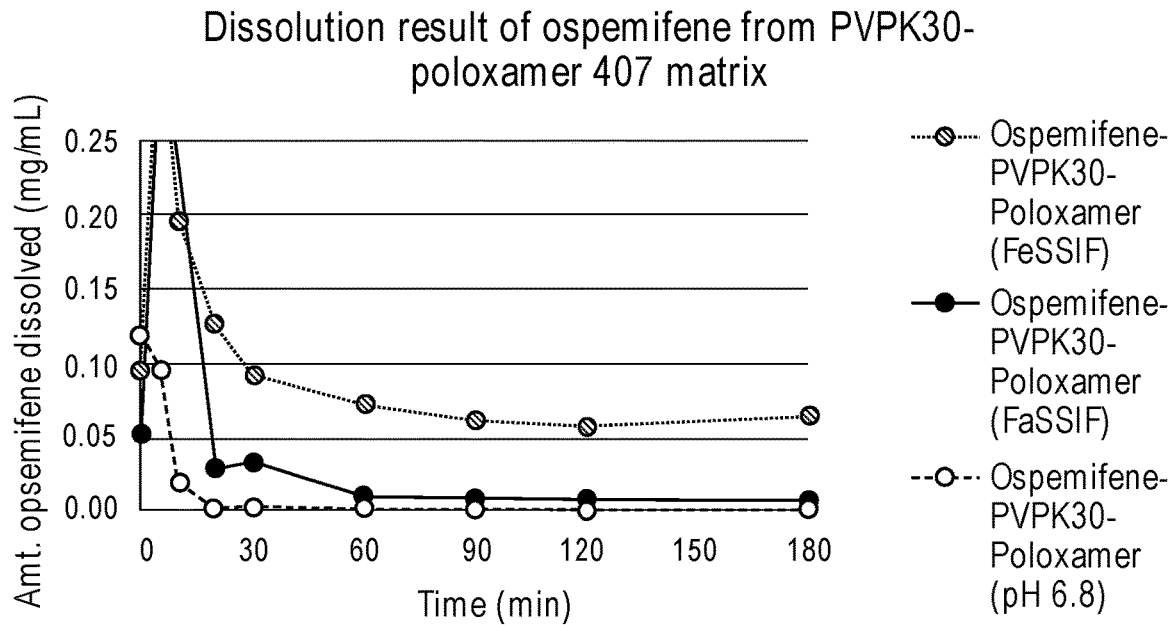
FIG. 22 depicts the dissolution kinetics of ospemifene from a solid dispersion comprising povidone (PVP K30) and poloxamer 407 (drug:carrier:surfactant 1:2:2) in FeSSIF, FaSSIF, and PBS, pH 6.8.
Figure 23:
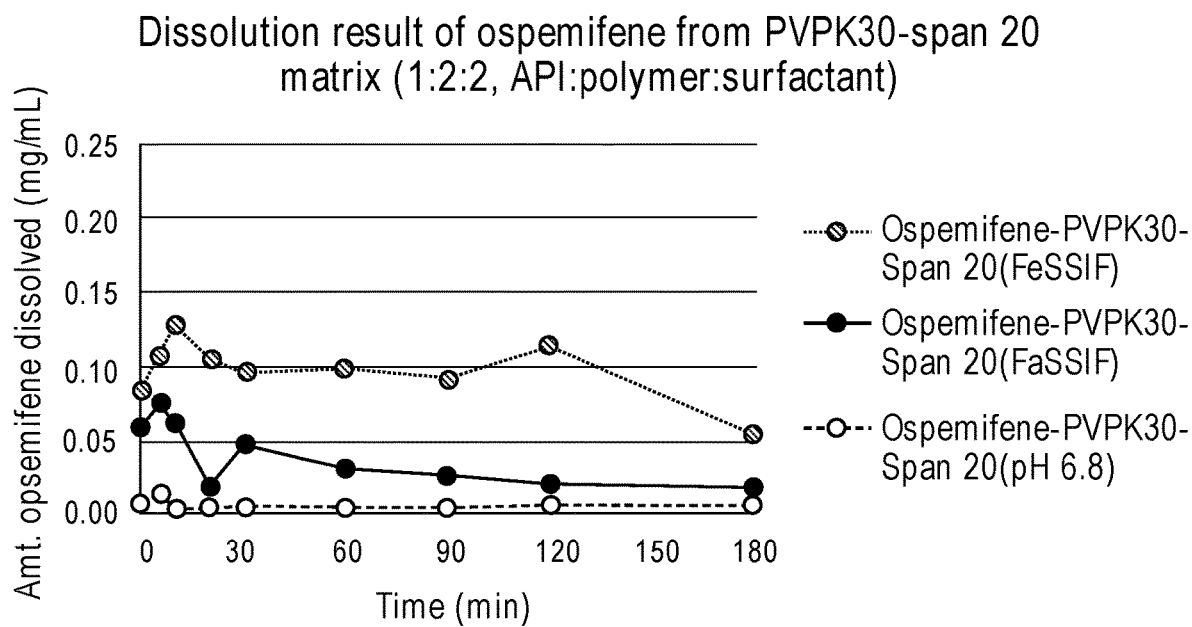
FIG. 23 depicts the dissolution kinetics of ospemifene from a solid dispersion comprising povidone (PVP K30) and Span 20 (drug:carrier:surfactant 1:2:2) in FeSSIF, FaSSIF, and PBS, pH 6.8.
Figure 24:
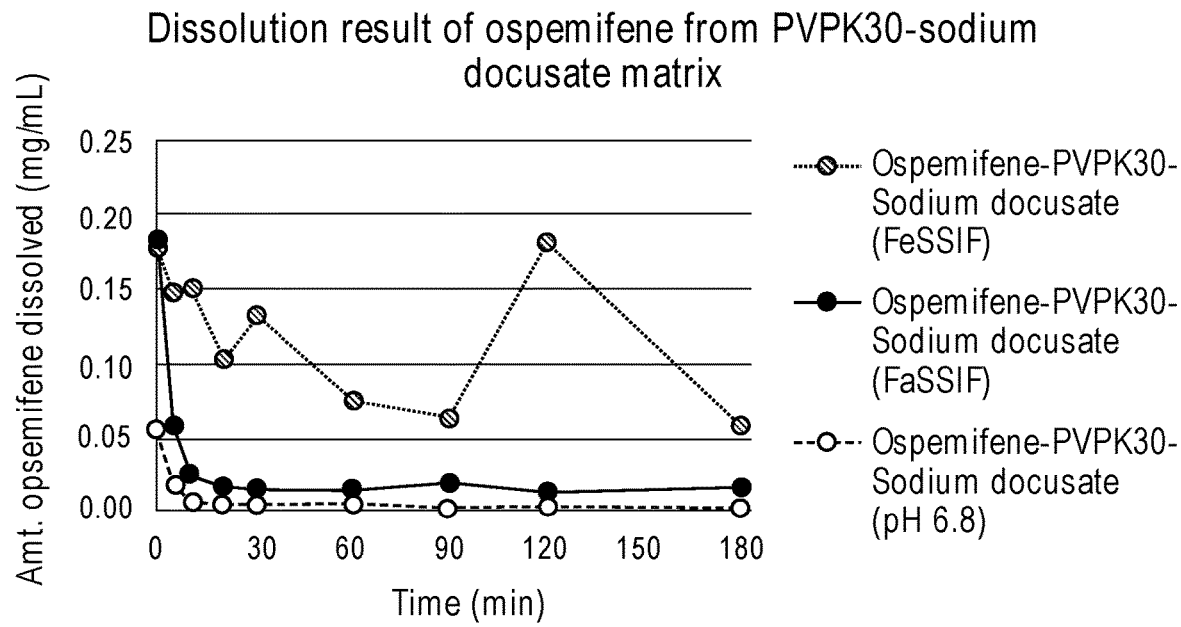
FIG. 24 depicts the dissolution kinetics of ospemifene from a solid dispersion comprising povidone (PVP K30) and sodium docusate (AOT) (drug:carrier:surfactant 1:2:2) in FeSSIF, FaSSIF, and PBS, pH 6.8.

To evaluate the effect of surfactant level on the dissolution profile of the ospemifene solid dispersions, a solid dispersion comprising ospemifene, povidone (PVP K30), and a surfactant (poloxamer 407, Span 20, and sodium docusate), where live level of surfactant was increased (drug:carrier:surfactant 1:2:2), were prepared and tested. At a target concentration of 0.24 mg mL, no significant improvement in the extent of dissolution was observed for solid dispersions comprising povidone and higher levels of surfactants. FIGS. 22-24.

Following the initial screening studies of ospemifene solid dispersions comprising a hydrophilic carrier or a hydrophilic carrier and surfactant, several formulations were selected for further characterization.

Certain formulations containing a non-ionic hydrophilic carrier (e.g., ospemifene, povidone, Span® 80 (1:3.4:0.6); ospemifene, copovidone, and Poloxamer 407 (1:2:2)) exhibited superlative dissolution kinetics. In-vitro dissolution studies indicated that ospemifene solid dispersion with copovidone and Poloxamer 407 (drug:carrier:surfactant 1:2:2) showed the highest extent of dissolution (about 0.15 mg/mL in FeSSIF and >0.03 mg/mL in FaSSIF and pH 6.8 buffer), which is about 2-6 time higher than that of micronized ospemifene under FeSSIF and FaSSIF. Ospemifere solid dispersion with povidone and Span® 80 (6:1) significantly prolonged drug supersaturation in all three media, particularly in pH 6.8 buffer (>0.01 mg/mL for more than 3 hrs).

Other formulations containing an enteric polymer-based hydrophilic carrier (e.g., ospemifene and HP-55 or ospemifene and HPMCAS) showed dissolution of >0.01 mg mL in all three media tested.

Ospemifene solid dispersions (20% drug loading) with copovidone, HP-55, copovidone/Poloxamer 407 (1:1), povidone/Span® 80 (6:1) were prepared both by hot melt extrusion and spray drying, as described above. These solid dispersions were analyzed by HPLC, stability. X-ray powder diffraction (XRPD), differential scanning calorimetry (DSC), and Fourier transform infrared spectroscopy (FTIR).

XRPD of hot-melt extrusion and spray dried formulations (both fresh samples and stressed) (stressed=40° C./75% RH for 5 days in closed amber container) were measured using Panalytical X'pert PRO. Samples were prepared with a zero background holder and XRPD data was obtained at room temperature.

The formulations all showed an amorphous halo in the x-ray diffractions except for the formulation containing poloxamer 407. The peaks observed in the ospemifene/copovidone/poloxamer solid dispersion appear to result from the liquid crystalline phase of the poloxamer 407, as confirmed by the presence of a melting peak in the DSC experiment (using DSC Q1000 from TA Instruments). The ospemifene in all formulations showed no XRPD crystallinity, indicating that the drug is in an amorphous state. The XRPD diffractograms for all three formulations showed no change after storage for 1 week in 40° C./75% RH.

Glass transition temperature and/or melting point temperature were evaluated for hot melt extrusion and spray-dried prepared ospemifene solid dispersions both freshly prepared and stressed (at 40° C./75% RH for 5 days in closed amber bottle) using DSC Q1000 from TA Instruments. Approximately 7-10 mg of each formulation was weighed and placed in an aluminum pan with a lid. The sample was heated at a rate of 10° C./min from 25° C. to 200° C. All freshly prepared hot melt extrusion and spray-dried ospemifene formulations exhibited a glass transition region except for the spray dried ospemifene/copovidone/poloxamer 407. Since most of the measured glass transition temperatures were around 50-60° C., the melting peak of poloxamer 407 in the spray dried formulation may have masked the glass transition. For all formulations prepared by both hot melt extrusion and spray drying method, no drug substance melting endotherm peak was found.

The glass transition temperatures of stressed spray dried formulations showed an increase from the originally measured temperatures. The porous nature of the spray dried material may have absorbed the water during the storage period. The water in the stability chamber could have acted as an anti-plasticizer in those instances.

TABLE IX

Glass Transition and Melting Points of Amorphous Samples

| Formulation type | | Tg, Tm (° C.) | Tg, Tm (° C., after stressed at 40° C./75% RH in closed condition) |
|---|---|---|---|
| Ospemifene-HP-55 | HME | Tg = 57.7, 77.1* | Tm = 63.6 |
| | SD | Tg = 61.2 | Tg = 69.12 |
| Ospemifene-copovidone | HME | Tg = 74.5 | Tg = 66.1 |
| | SD | Tg = 69.8 | Tg = 76.25 |
| Ospemifene-copovidone-poloxamer 407 | HME | Tg = 91.8 Tm = 49.3 | Tg = 161.7 Tm = 49.8 |
| | SD | Tm = 52.3 | Tm = 52.2 |
| Ospemifene-povidone-Span80 | HME | Tg = 51.7, 129.2* | Tg = 63.0, 125.8* |
| | SD | Tg = 55.6 | Tg = 57.4 |

*Two values indicate two amorphous phases exist.

FTIR spectra were collected from freshly prepared hot melt extrusion and spray-dried ospemifene formulations, as well as ospemifene and excipients used in the formulations using a Perkin Elmer Spectrum One with an attenuated total reflectance (ATR) accessory. An FTIR spectrum was collected from 4000-600 $cm^{-1}$ with 4 scans per sample at room temperature.

The strongest peak measured by FTIR from ospemifene was from the alkyl halide bond of chloride and carbon at around 700 $cm^{-1}$. To determine whether any interaction between the drug and hydrophilic carrier and/or surfactant were present, the alkyl halide peak shift was used as an indicator. Results showed that the alkyl halide peak of spray dried ospemifene with copovidone shifted upward to 705 $cm^{-1}$ indicating a weaker interaction with the chloride and hydrogen from the copovidone. On the other hand, the alkyl halide peak from the HME processed ospemifene-HP-55 solid dispersion showed a downward shift to 701 $cm^{-1}$.

TABLE X

FITR Analysis

| Formulation type | | C—Cl peak observed ($cm^{-1}$) | Indication of drug-polymer interaction |
|---|---|---|---|
| Ospemifene-HP-55 | HME | 701 | stronger |
| | SD | 703 | Moderate |
| Ospemifene-PVPVA64 | HME | 703 | Moderate |
| | SD | 705 | weaker |
| Ospemifene-PVPVA64-poloxamer 407 | HME | 703 | Moderate |
| | SD | 704 | Moderate/stronger |
| Ospemifene-PVPK30-span80 | HME | 703 | Moderate |
| | SD | 703 | Moderate |

The following ospemifene solid dispersions were prepared using the hot melt extrusion and spray drying procedures described above;
  Ospemifene/copovidone (PVPVA64);
  Ospemifene/copovidone (PVPVA64)/poloxamer 407;
  Ospemifene/HP-55; and
  Ospemifene/povidone (PVP K30)/Span 80.

These formulations were then stored at 40° C. and 75% RH (open conditions) for 78 hours and analyzed by HPLC. The HPLC results showed the ospemifene is generally chemically compatible with all of the excipients tested, with the exception of HP-55, as used in the hot melt extrusion method of preparation. Preparing the ospemifene/HP-55 solid dispersion by hot melt extrusion resulted in the highest amount of impurity (about 7%), however, preparing the same formulation by spray drying resulted in much less impurity (about 1%), indicating that different production methods can affect the amount of impurity present in the solid dispersion. All other solid dispersions tested had total impurities of 0.34% or less, with the hot melt extrusion and spray dried processed ospemifene/copovidone/poloxamer formulation having the least amount of impurities (0.18% and 0.17%, respectively).

Example 6: USP II Dissolution Study

A large scale dissolution study was conducted using a USP apparatus 2 with a paddle with 500 mL of either FeSSIF or FaSSIF solution maintained at 37° C. and with the paddle speed set to 50 RPM. Ospemifene solid dispersions comprising 1) copovidone (PVPVA64) and poloxamer 407 2) HP-55, 3) povidone and Tween 80, and 4) copovidone (PVPVA64) were prepared by both the hot melt extrusion and spray drying techniques described above. A sample of ground Osphena® tablets was also prepared. The samples were added as powder form and the target concentration was 0.24 mg/mL (120 mg in 500 mL). Dissolution media was drawn at 30 minutes, 1, 2 and 3 hour(s) and centrifuged at 14000 rpm for one minute. Then 50 μL of supernatant was transferred to an HPLC vial and diluted with 50 μL acetonitrile and analyzed by HPLC as described above.

Figure 25:
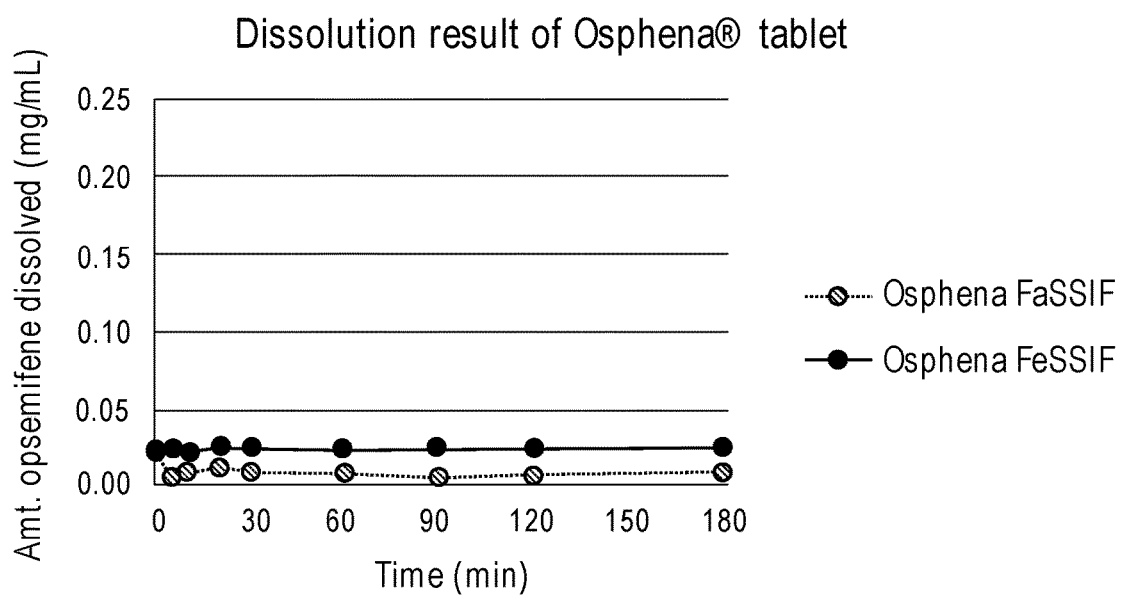
FIG. 25 depicts the dissolution kinetics of Osphena® granules in FeSSIF and FaSSIF.
Figure 26:
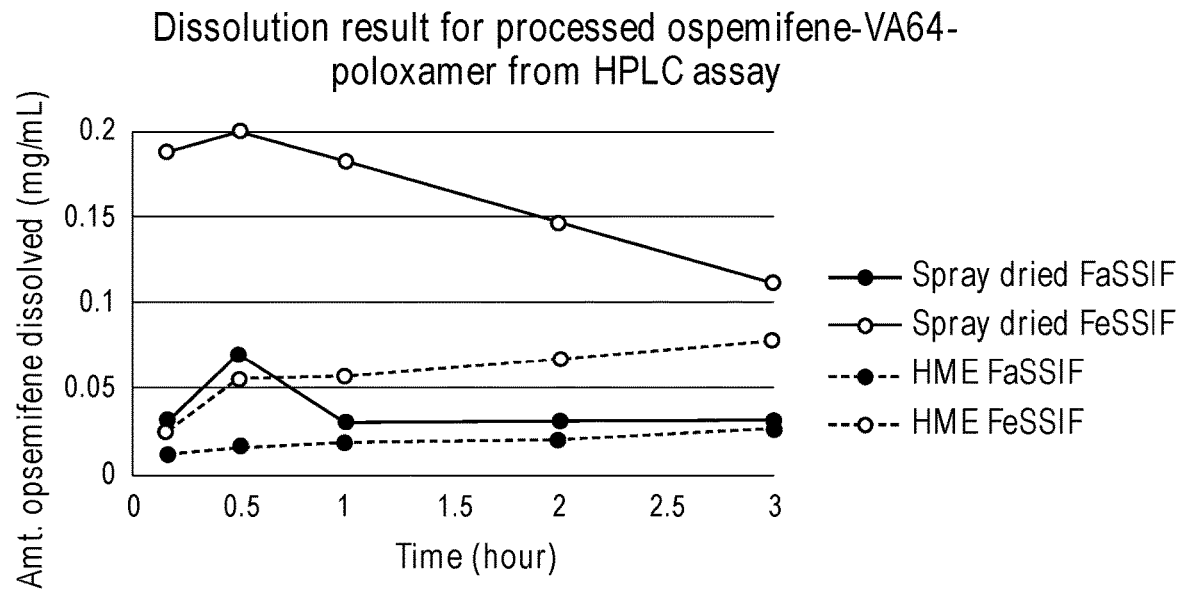
FIG. 26 depicts the dissolution kinetics of ospemifene from solid dispersions comprising copovidone (PVPVA 64) and poloxamer 407 in FeSSIF and FaSSIF, where the solid dispersions are made by either a spray drying or hot melt extrusion technique.

The dissolution results for ground Osphena® tablets are shown in FIG. 25. For the solid dispersion comprising ospemifene, copovidone, and poloxamer 407, the spray dried formulation showed a greater extent of dissolution than the formulation prepared by hot melt extrusion. FIG. 26. The dissolution of the spray-dried formulation was about 3 times higher than the dissolution of Osphena® tablet granules in both FaSSIF and FeSSIF.

Figure 27:
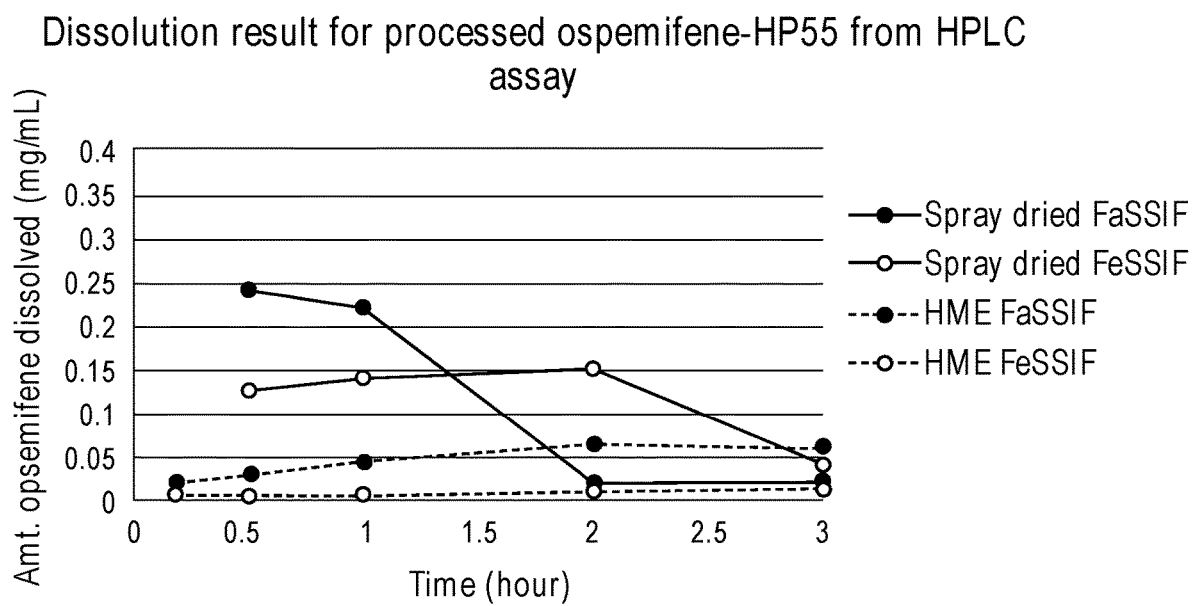
FIG. 27 depicts the dissolution kinetics of ospemifene from solid dispersions comprising HP-55 in FeSSIF and FaSSIF, where the solid dispersions are made by either a spray drying or hot melt extrusion technique.

For the HP-55 solid dispersion, the spray dried formulation showed a greater extent of dissolution than the formulation prepared by hot melt extrusion. In FaSSIF, the HP-55 solid dispersion made by spray drying had a very fast rate of dissolution and maintained a supersaturated stale for at least 1 hour before returning to a base line of 0.02 mg/mL, which is about 2 times higher than the dissolution of Osphena® tablet granules in FaSSIF. FIG. 27. In FaSSIF, the HP-55 solid dispersion made by spray drying also had a higher extent of supersaturation than the sample prepared by hot melt extrusion.

Figure 28:
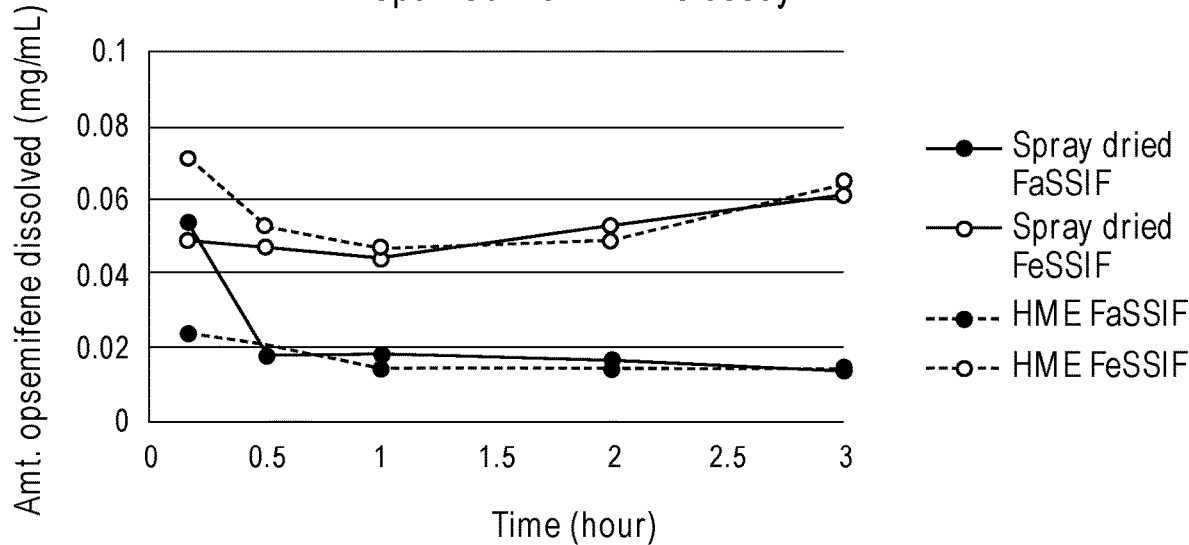
FIG. 28 depicts the dissolution kinetics of ospemifene from solid dispersions comprising povidone (PVP K30) and Span 80 in FeSSIF and FaSSIF, where the solid dispersions are made by either a spray drying or hot melt extrusion technique.

For the solid dispersion comprising ospemifene, povidone (PVP K30), and Span 80, both the spray dried and hot melt extrusion formulations showed similar dissolution profiles in FaSSIF and FeSSIF. FIG. 28. The dissolution of this formulation was about 2 times higher than the dissolution of Osphena® tablet granules in both FaSSIF and FeSSIF.

Figure 29:
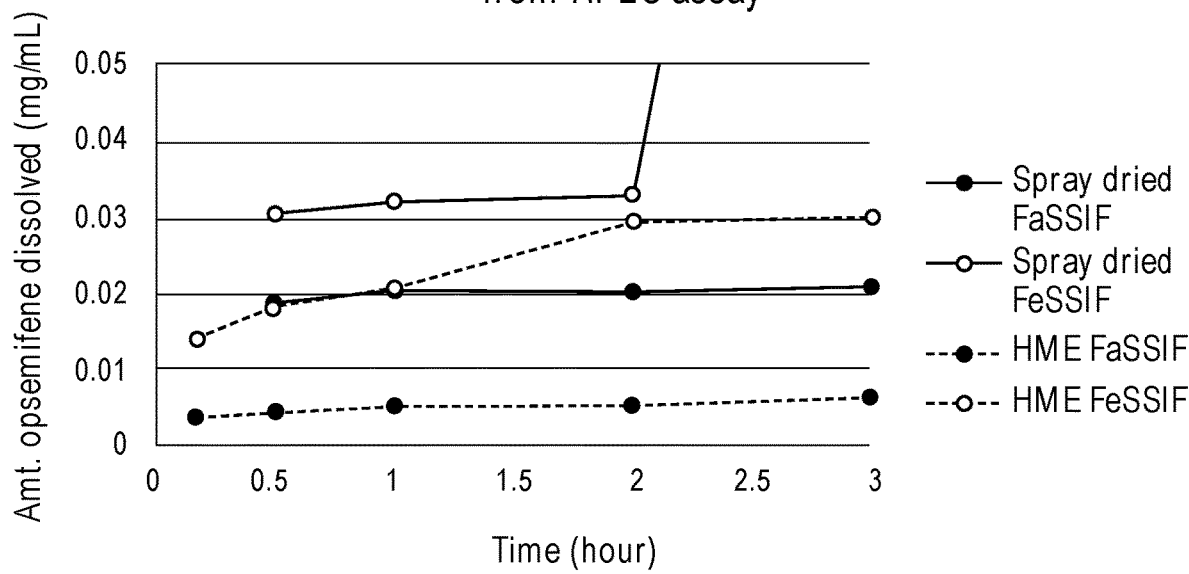
FIG. 29 depicts the dissolution kinetics of ospemifene from solid dispersions comprising copovidone (PVPVA 64) in FeSSIF and FaSSIF, where the solid dispersions are made by either a spray drying or hot melt extrusion technique.

For the solid dispersion comprising ospemifene and copovidone, the spray dried formulation showed a greater extent of dissolution than the formulation made by hot melt extrusion. The copovidone solid dispersion made by hot melt extrusion showed increased dissolution in FeSSIF as compared to FaSSIF. FIG. 29.

Using these methods and compositions it will now be possible to produce suitable dosage forms of ospemifene that provide improved performance as compared to previous formulations, which require administration of 60 mg per day. For example, it may be possible to achieve therapeutically effective levels using ospemifene solid dispersion dosage forms in amounts of less than 60 mg per day.

While this invention has been particularly shown and described with references to preferred embodiments thereof, it will be understood by those skilled in the art that various changes in form and details may be made therein without departing from the scope of the invention encompassed by the appended claims.

BIBLIOGRAPHY

The following references are hereby incorporated by reference herein in their entireties:

Charman, S. A. & Charman, W. N. (2003). Oral modified-release delivery systems. In *Modified-Release Drug Delivery Technology*, Eds. Rathbone, N J. et al. eds, Marcel Dekker, pp. 1-10.

Curatolo W, Nightingale J A, & Herbig S M. (2009). Utility of hydroxypropylmethylcellulose acetate succinate (HPMCAS) for initiation and maintenance of drug supersaturation in the GI milieu. Pharm Res. 26(6): 1419-1431.

Janssens, S. & Mooter, G. V. D. (2009). Review: physical chemistry of solid dispersions. *J. Pharm. Pharmacol.* 61: 1571-1586.

Kangas L (1990). Biochemical and pharmacological effects of toremifene metabolites. *Cancer Chemother. Pharmacol.* 27: 8-12.

Koskimies, P. et al. (2013). Single-dose and steady-state pharmacokinetics of ospemifene, a selective estrogen modulator, in post-menopausal women. *Int. J. Clin. Pharmacol. Ther.* 51(11): 861-867.

Kostwicz, E. S., Brauns, U., Becker, R., and Dressman, J. B. (2002). Forecasting the oral absorption behavior of poorly soluble weak bases using solubility and dissolution studies in biorelevant media. *Pharm. Res.,* 19(3): 345-349.

Leuner, C. & Dressman, L. (2000). Improving drug solubility for oral delivery using solid dispersions. *Eur. J. Pharm. Biopharm.* 50:47-60.

Payer. L. (1991). The menopause in various cultures. In: *A portrait of the menopause. Export reports on medical and therapeutic strategies for the 1990s.* eds. Berger, H. and Boulet, M., Parthenon Publishing, Park Ridge N.J. USA, pp. 3-22.

Rekers, H. (1991). Matering the menopause. In: *A portrait of the menopause. Export reports on medical and therapeutic strategies for the 1990s.* eds. Berger, H. and Boulet, M., Parthenon Publishing. Park Ridge N.J. USA, pp. 23-43.

Serajuddin, A. T. M. (1999). Solid dispersion of poorly water-soluble drugs: early promise, subsequent problems, and recent breakthroughs. *J. Pharm. Sci.* 88(10): 1058-1066.

Sun D D, Ju T R, Lee P I. (2012). Enhanced kinetic solubility profiles of indomethacin amorphous solid dispersions in poly(2-hydroxylethyl methacrylate) hydrogels. *Eu. J. Pharm. Biopharm.* 81: 149-158.

Tanno F, Nishiyama Y, Kokubo H, Obara S. (2004). Evaluation of hypromellose acetate succinate (HPMCAS) as a carrier in solid dispersions. *Drug Dev. Ind. Pharm.* 30(1): 9-17.

Vasconelos et al., (2007). Solid dispersions as strategy to improve oral bioavailability of poor water soluble drugs. *Drug Discovery Today,* 12:1068-1075.

van Drooge, D. J. et al. (2006). Characterization of the molecular distribution of drugs in glassy solid dispersions at the nan-meter scale, using differential scanning calorimetry and gravimetric water vapour techniques. *Int. J. Pharm.* 310:220-229.

The invention claimed is:

1. A solid dispersion composition in a solid state composition comprising a solid dispersion of ospemifene, wherein the solid dispersion comprises:
   ospemifene; and
   a hydrophilic carrier selected from the group consisting of copovidone, polyvinylpyrrolidone, a polyvinylpyrrolidone/vinyl acetate co-polymer, hydroxyl propyl methylcellulose, hypromellose acetate succinate, a methacrylic acid copolymer, hydroxypropylcellulose, a polyvinyl caprolactam-polyvinyl acetate polyethylene glycol graft co-polymer, hydroxypropyl methylcellulose phthalate, and mixtures thereof,
   wherein the solid dispersion is in a solid state.

2. The composition of claim 1, wherein the ratio of ospemifene to the hydrophilic carrier is in a range of about 1:1 to about 1:20 (w/w).

3. The composition of claim 1, wherein the ratio of ospemifene to the hydrophilic carrier is about 1:4 (w/w).

4. The composition of claim 1, wherein the solid dispersion further comprises a surfactant.

5. A pharmaceutical composition comprising the composition of claim 1 and a pharmaceutically acceptable excipient.

6. The pharmaceutical composition of claim 5, wherein the pharmaceutical composition is provided in a dosage form.

7. The pharmaceutical composition of claim 5, wherein the pharmaceutically acceptable excipient comprises at least one of a glidant, a dispersant, an enteric coating, a lubricant, a binder, or a buffering agent.

8. The pharmaceutical composition of claim 5, wherein the hydrophilic carrier and surfactant are combined in a ratio ranging from 1:1 to 1:6.

9. The pharmaceutical composition of claim 5, wherein the pharmaceutically acceptable excipient is selected from at least one of colloidal silicon dioxide, lactose monohydrate, magnesium stearate, mannitol, microcrystalline cellulose, polyethylene glycol, pregelatinized starch, sodium starch glycolate, titanium dioxide, triacetin, and triose, and mixtures thereof.

10. The pharmaceutical composition of claim 5, wherein after a single administration in a human subject of the pharmaceutical composition there is greater bioavailability or no difference in the bioavailability of ospemifene when the composition is administered to the subject in a fasted versus a fed state.

11. The composition of claim 1, wherein the hydrophilic carrier is a polyvinylpyrrolidone/vinyl acetate co-polymer.

12. The composition of claim 1, wherein the ospemifene is amorphous.

13. The composition of claim 1, wherein the hydrophilic carrier is selected from the group consisting of a polyvinylpyrrolidone/vinyl acetate co-polymer, hypromellose acetate succinate, hydroxypropylcellulose, a polyvinyl caprolactam-polyvinyl acetate polyethylene glycol graft co-polymer, and hydroxypropyl methylcellulose phthalate.

* * * * *